United States Patent
Donnelly et al.

(10) Patent No.: US 10,106,519 B2
(45) Date of Patent: Oct. 23, 2018

(54) 3-PHENYL-7-HYDROXY-ISOCOUMARINS AS MACROPHAGE MIGRATION INHIBITORY FACTOR (MIF) INHIBITORS

(71) Applicant: The Provost, Fellows, Foundation Scholars, & the Other Members of Board, of The College of The Holy, Dublin (IE)

(72) Inventors: Seamas Donnelly, Mount Merrion (IE); David Lloyd, Adelaide (AU); Ciaran O'Reilly, Dublin (IE); Darren Fayne, Dublin (IE)

(73) Assignee: The Provost, Fellows, Foundation Scholars, and the Other Members of Board, of the College of the Holy and Undivided Trinity of Queen Elizabeth, Near Dublin (IE)

( * ) Notice: Subject to any disclaimer, the term of this patent is extended or adjusted under 35 U.S.C. 154(b) by 13 days.

(21) Appl. No.: 15/129,593

(22) PCT Filed: Mar. 27, 2015

(86) PCT No.: PCT/EP2015/056791
§ 371 (c)(1),
(2) Date: Sep. 27, 2016

(87) PCT Pub. No.: WO2015/144911
PCT Pub. Date: Oct. 1, 2015

(65) Prior Publication Data
US 2017/0144983 A1    May 25, 2017

(30) Foreign Application Priority Data
Mar. 28, 2014 (GB) .................................. 1405644.4

(51) Int. Cl.
*C07D 311/76* (2006.01)
(52) U.S. Cl.
CPC .................................. *C07D 311/76* (2013.01)
(58) Field of Classification Search
None
See application file for complete search history.

(56) References Cited

U.S. PATENT DOCUMENTS

2007/0270395 A1    11/2007   Sircar et al.

FOREIGN PATENT DOCUMENTS

WO    2012142498 A2    10/2012

OTHER PUBLICATIONS

Bacher et al.; "An essential regulatory role for macrophage migration inhibitory factor in T-cell activation"; Proc. Natl. Acad. Sci. USA; 1996; pp. 7849-7854; vol. 93.
Bernhagen et al.; "Purification, Bioactivity, and Secondary Structure Analysis of Mouse and Human Macrophage Migration Inhibitory Factor (MIF)"; Biochemistry; 1994; pp. 14144-14155; vol. 33:47.
Cai et al.; "Assembly of 3-Substituted Isocoumarins via a Cul-Catalyzed Domino Coupling/Addition/Deacylation Process"; The Journal of Organic Chemistry; 2012; pp. 2331-2336; vol. 77.
De Angelis et al.; "Isocoumarins as estrogen receptor beta selective ligands: Isomers of isoflavone phytoestrogens and their metabolites"; Bioorganic & Medicinal Chemistry; 2005; pp. 6529-6542; vol. 13:23.
Kamimura et al.; "Intracellular Distribution of Macrophage Migration Inhibitory Factor Predicts the Prognosis of Patients with Adenocarcinoma of the Lung"; Cancer; 2000; pp. 334-341; vol. 89:2.
Lubetsky et al.; "The Tautomerase Active Site of Macrophage Migration Inhibitory Factor is a Potential Target for Discovery of Novel Anti-inflammatory Agents"; The Journal of Biological Chemistry; 2002; pp. 24976-24982; vol. 277:28.
Meyer-Siegler et al.; "Enhanced Expression of Macrophage Migration Inhibitory Factor in Prostatic Adenocarcinoma Metastases"; Urology; 1996; pp. 448-452; vol. 48:3.
Meyer-Siegler et al.; "Inhibition of Macrophage Migration Inhibitory Factor or Its Receptor (CD74) Attenuates Growth and Invasion of DU-145 Prostate Cancer Cells"; The Journal of Immunology; 2006; pp. 8730-8739; vol. 177:12.
Mitchell et al.; "Sustained Mitogen-activated Protein Kinase (MAPK) and Cytoplasmic Phospholipase A2 Activation by Macrophage Migration Inhibitory Factor (MIF)"; The Journal of Biological Chemistry; 1999; pp. 18100-18106; vol. 274:25.
Rose et al.; "Oxygen Heterocycles. Part XI. The Condensation of Phenols with Homophthalic Acids and Anhydrides"; J. Chem Soc.; 1965; pp. 6100-6104.
Takahashi et al.; "Involvement of Macrophage Migration Inhibitory Factor (MIF) in the Mechanism of Tumor Cell Growth"; Molecular Medicine; 1998; pp. 707-714; vol. 4:11.
Won-Jea Cho et al.; "Synthesis and Comparative Molecular Field Analysis (CoMFA) of Antitumor 3-Arylisoquinoline Derivatives"; Bioorganic & Medicinal Chemistry; 1998; pp. 2449-2458; vol. 6:12.

*Primary Examiner* — Po-Chih Chen
(74) *Attorney, Agent, or Firm* — The Webb Law Firm

(57) ABSTRACT

Provided herein are 3-phenyl-7-hydroxy-isocoumarin compounds which are MIF inhibitors; compositions comprising said inhibitors and methods for treating or preventing diseases associated with MIF.

18 Claims, 11 Drawing Sheets

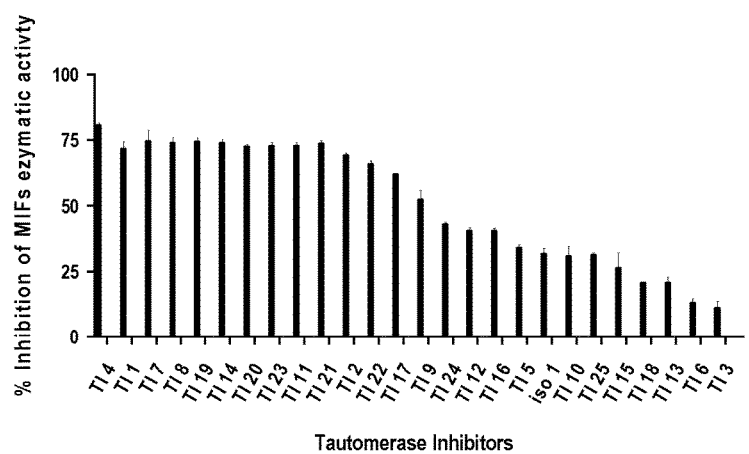
Figure 1: Inhibition of MIF tautomerase enzymatic activity
Inhibition was calculated as the reduction of the rate of change of the tautomerase reaction with the addition of the inhibitor averaged over five minutes.

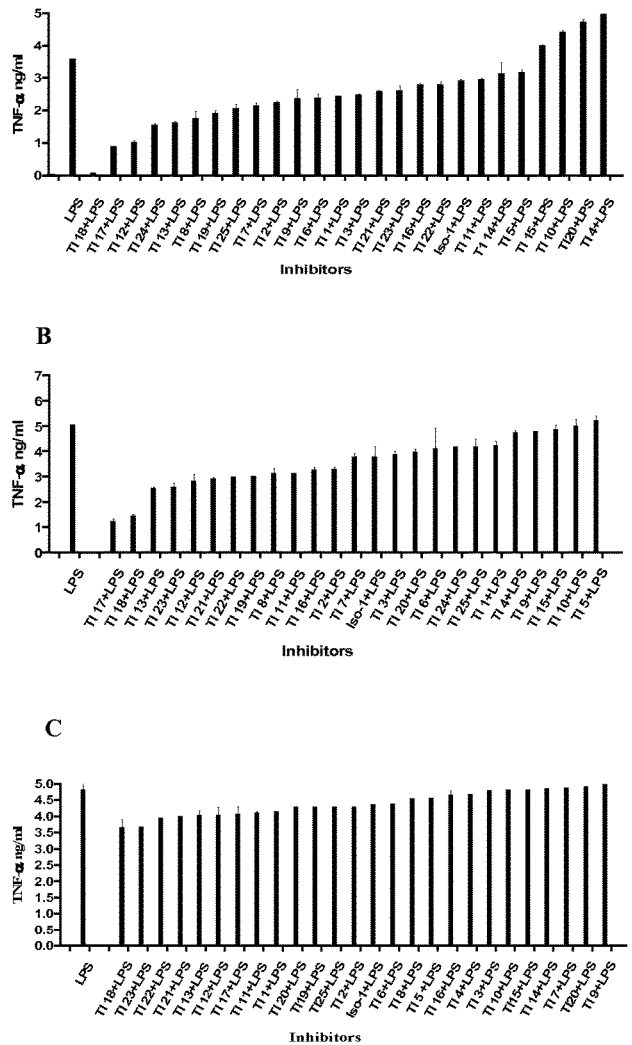

Figure 2: Inhibition of LPS induced TNF-α production

A RAW macrophage cells were plated at 1 X 10$^5$ per well and pre-treated with the inhibitors at 100μM for 30 minutes prior to stimulation with 100ng/ml LPS. After 16 hours, supernatants were collected and assessed for levels of TNF- α using TNF- α ELISA kit. B Raw cells were pre-treated with 50μM of each inhibitor 30 minutes prior to LPS stimulation and supernatants were assessed after 16 hours for TNF-α level. C RAW cells were pre-treated with 10μM of Tautomerase inhibitors 30 minutes prior to LPS stimulation. Data are presented as mean and SEM (n=6).

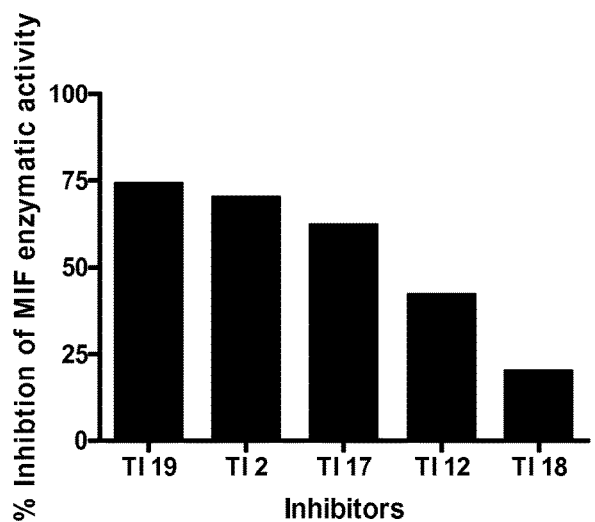
Figure 3: Inhibition of MIF tautomerase enzymatic activity of 5 exemplary compounds
Inhibition seen with 100 ng/ml MIF with its substrate L-dopachrome incubated with each of the inhibitors at 100μM measured with a spectrophotometer over 20 minutes.

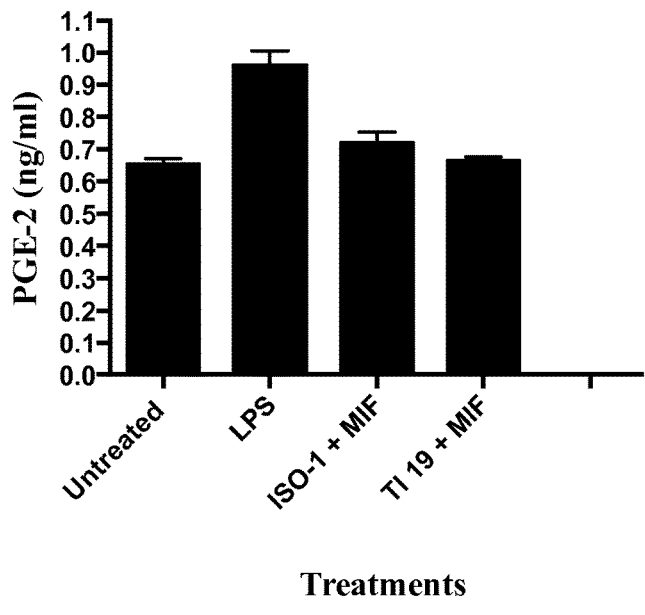

Figure 4: Inhibition of MIF induced PGE-2

RAW macrophage cells were plated at a cell density at $1 \times 10^5$ per well and were pre-treated with four of the tautomerase inhibitors and then treated with 100ng/ml of LPS overnight at 37°C in a humidified 5% $CO_2$ incubator. RAW cells were treated with 100μM of inhibitors as indicated. Supernatants were assessed using PGE-2 ELISA kit. ISO-1, the commercially available inhibitor of MIF was also included. ($p < 0.05$, $p > 0.01$, Data presented as mean and SEM (n=6)).

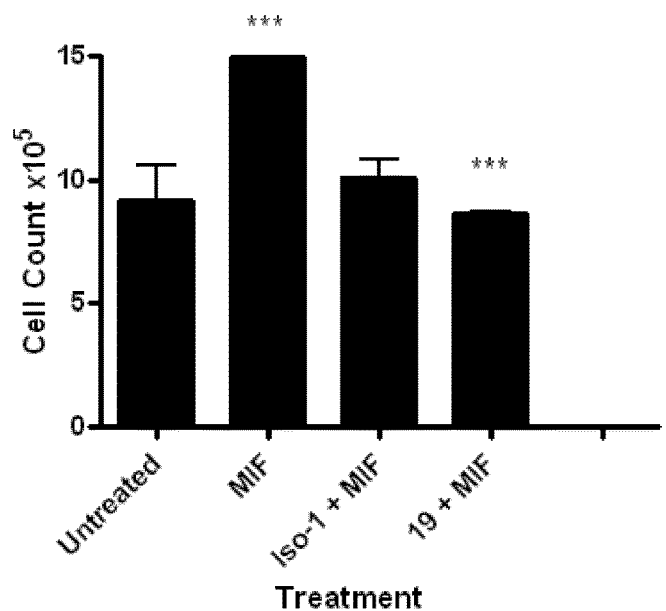
Figure 5: Inhibition of MIF enzymatic activity reduces cell proliferation.
100ng/ml of rMIF significantly promotes proliferation of LLC compared to untreated LLC cells. Proliferation is inhibited significantly in the presence of 100μM of TI 19 and TI 17 but not ISO-1. (*** $p < 0.001$, Data presented as mean + SEM, n=6)

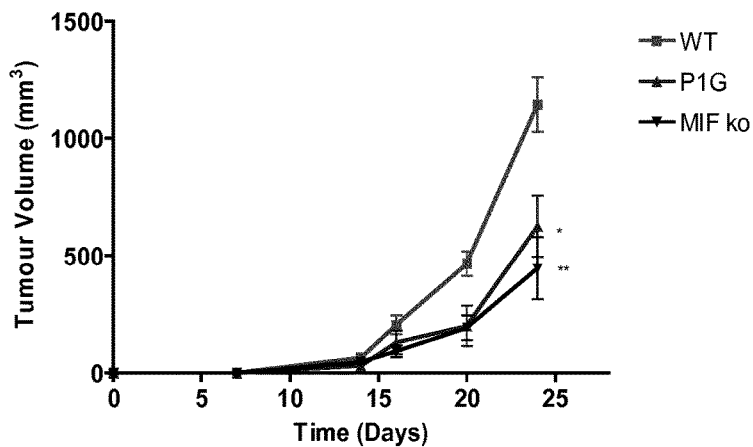
Figure 6: Lewis lung cell tumour volume is significantly lower in MIF-KO and MIF-P1G mice compared to wild type
Lewis Lung carcinoma cells ($5 \times 10^5$) were injected sub-cutaneously into the left flank of C57BL/6 WT mice, P1G and MIF KO mice. Caliper measurements were taken twice weekly and tumour volume ($mm^3$) was calculated as $0.5 \times L \times W^2$ (n=4)

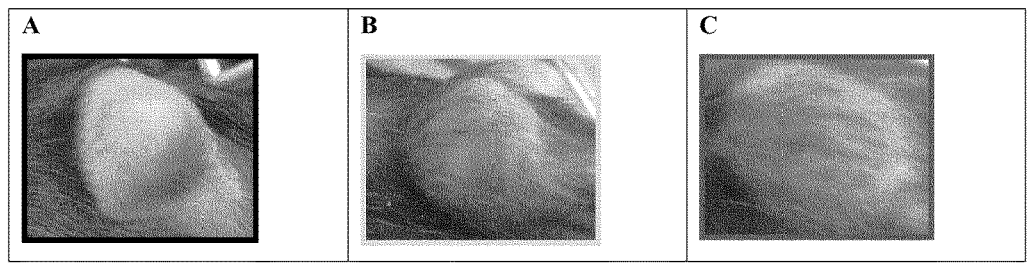
Figure 7: Gross appearance of subcutaneous tumours. Appearance of subcutaneous tumours at day 24 of model. (A) Untreated; (B) 5% DMSO vehicle: and (C) TI 19 treatment (35mg/kg).

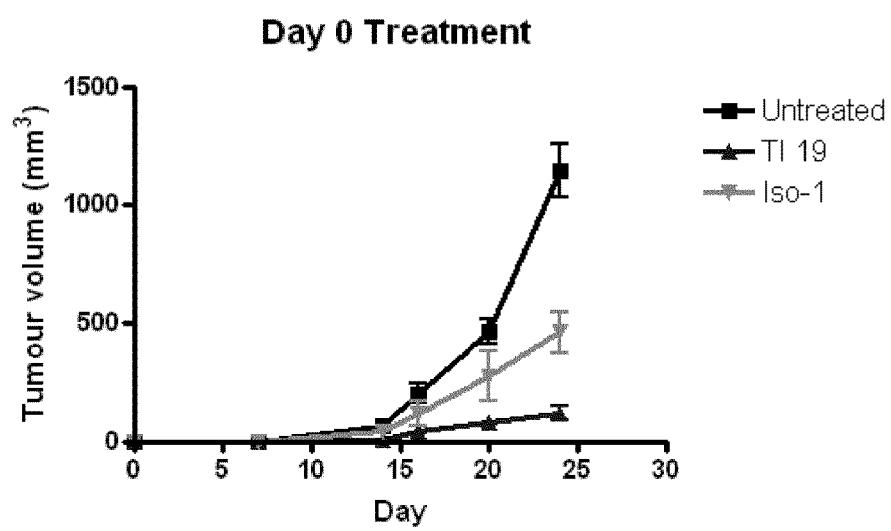

Figure 8: Inhibition of MIF tautomerase activity attenuates tumour growth. Lewis Lung carcinoma cells ($5 \times 10^5$) were injected sub-cutaneously into the left flank of C57BL/6 mice. Animals were injected intraperitoneally 30min prior to tumour inoculation and twice weekly thereafter, with 35mg/kg TI (tautomerase inhibitor solubilized in DMSO) or as indicated. Caliper measurements were taken twice weekly and tumour volume ($mm^3$) was calculated as $0.5 \times L \times W^2$. (**$p < 0.01$, n=4)

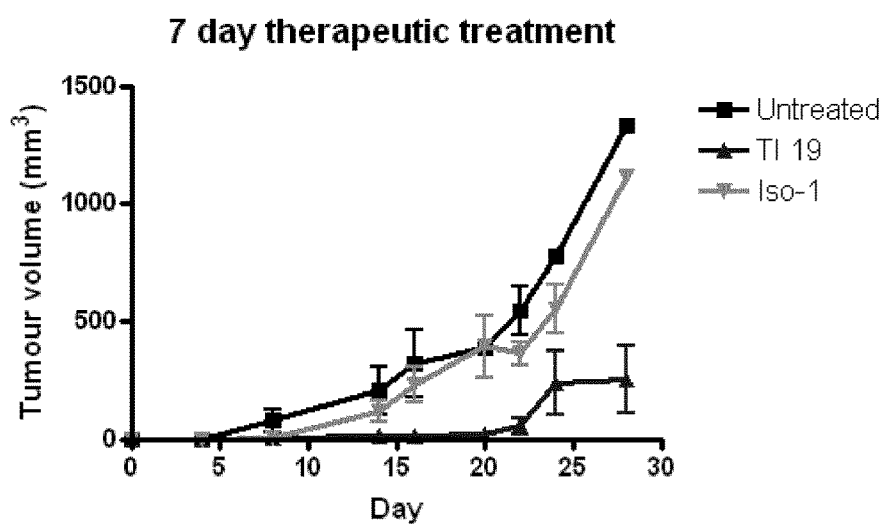

Figure 9: Inhibition of MIF tautomerase activity attenuates tumour growth. Lewis Lung carcinoma cells ($5 \times 10^5$) were injected sub-cutaneously into the left flank of C57BL/6 mice. Once the tumour had become palpable on the flank of the mouse (7-8 days after innoculation), the animals were injected intraperitoneally and twice weekly thereafter, with 35mg/kg TI (tautomerase inhibitor solubilized in DMSO) or as indicated. Caliper measurements were taken twice weekly and tumour volume ($mm^3$) was calculated as $0.5 \times L \times W^2$. (**$p < 0.01$, n=4)

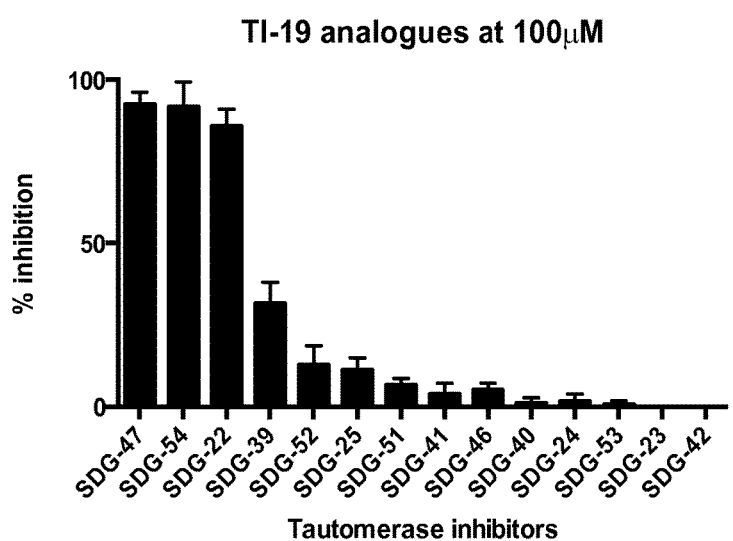
Figure 10: Inhibition of MIF tautomerase enzymatic activity. Inhibition was calculated as the reduction of the rate of change of the tautomerase reaction with the addition of the inhibitor averaged over five minutes.

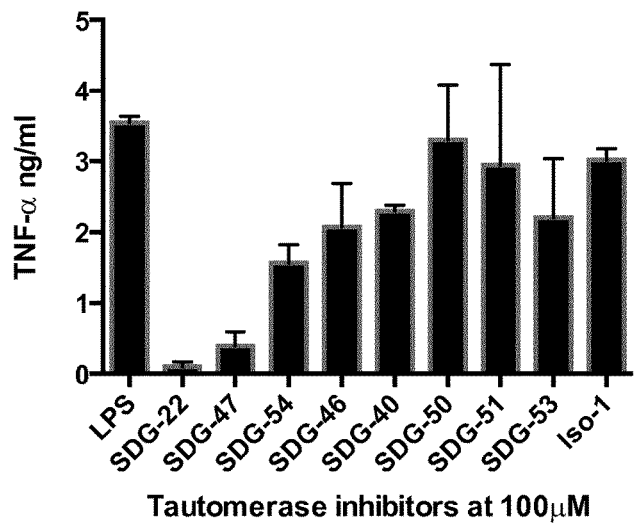
Figure 11: Inhibition of LPS induced TNF-α production. RAW macrophage cells were plated at 1 X $10^5$ per well and pre-treated with the inhibitors at 100μM for 30 minutes prior to stimulation with 100ng/ml LPS. After 16 hours, supernatants were collected and assessed for levels of TNF- α using TNF- α ELISA kit.

3-PHENYL-7-HYDROXY-ISOCOUMARINS AS MACROPHAGE MIGRATION INHIBITORY FACTOR (MIF) INHIBITORS

CROSS-REFERENCE TO RELATED APPLICATIONS

This application is the United States national phase of International Application No. PCT/EP2015/056791 filed Mar. 27, 2015, and claims priority to United Kingdom Patent Application No. 1405644.4 filed Mar. 28, 2014.

FIELD OF THE INVENTION

The present invention relates to the development of inhibitors of macrophage migration inhibitory factor (MIF) and the utility of said inhibitors in the treatment of cancer.

BACKGROUND TO THE INVENTION

The orphan cytokine, macrophage migration inhibitory factor (MIF), is a pleiotropic, pro-inflammatory mediator, released by numerous cell types including endothelial cells, eosinophils, macrophages, lymphocytes and neutrophils. MIF exerts numerous biological effects and plays a key role in the inflammatory and autoimmune processes through the induction of TNF-α, IL-1, IL-8, cyclooxygenase and nitric oxide release by macrophages. Furthermore, MIF is involved in the down regulation of the oncogenic protein p53 and can counter act the production of glucocorticoids. Consequently, MIF has been implicated in the pathogenesis of a number of inflammatory disease states including sepsis, atherosclerosis, lupus, rheumatoid arthritis, asthma, glomerulonephritis and acute respiratory distress syndrome (ARDS). Its role in cancer biology has also recently been highlighted. Unusually for a cytokine, MIF contains a well-defined enzymatic site, which acts as a keto-enol tautomerase. It is believed that this tautomerase site plays a role in the numerous biological effects displayed by MIF.

MIF exists as a symmetrical trimer consisting of 3 repeating, 12.5 KDa, 114 residue subunits each with β-α-β homology. Unusually, aside from its role as a cytokine, MIF also displays two distinct catalytic activities: a keto-enol tautomerase and a thiol mediated oxidoreductase. The MIF trimer consists of three hydrophobic keto-enol tautomerase active sites which each span two subunits. The N-terminal proline residue of each subunit resides within the active site and displays a low $pK_a$ of around 5.6-6. The nucleophilic character of this residue enables it to catalyze the isomerization of a number of substrates including 4-hydroxy phenyl pyruvate (HPP), phenyl pyruvic acid and D-Dopachrome.

MIF is overexpressed in numerous cancers including lung cancer, ovarian cancer, breast cancer, hepatocellular cancer, oesophageal squamous-cell cancer, bladder cancer, cervical squamous-cell cancer, pancreatic cancer, glioblastomas, prostate cancer, osteosarcoma, colorectal cancer, head and neck cancer and malignant melanoma, gastric cancer, glioma, nasopharyngeal cancer.

As a key player in several cancers, clearly the development of novel inhibitors of MIF, which could potentially serve as chemotherapeutics in the treatment of the aforementioned disease states is highly desirably.

In WO2012142498, Gaweco describes quinolinone compounds which demonstrate MIF inhibitory activity.

Similarly, in US2007270395 Jagadish describes quinolinone compounds and quinoline compounds which demonstrate MIF inhibitory activity. Said compounds are said to have utility in the treatment of inflammatory bowel disease.

SUMMARY OF THE INVENTION

In one aspect, the present invention provides a compound having the formula

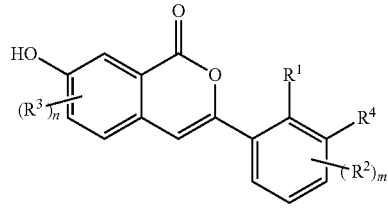

wherein n is 0 to 3; m is 0 to 3;

$R^1$ and $R^4$ are the same or different and are independently selected from the group consisting of hydrogen, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;

wherein $R^1$ and $R^4$ can independently be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl;

$R^2$ is independently selected from the group consisting of hydrogen, a hydroxyl, an amino group, a halogen, a cyano group, a nitro group, a nitroso group, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic, $C_1$-$C_{12}$ alkoxy;

$R^3$ is independently selected from the group consisting of hydrogen, a hydroxyl, an amino group, a halogen, a cyano group, a nitro group, a nitroso group, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;

wherein, independently any $R^2$ or $R^3$ can be unsubstituted, or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;

wherein $R^1$ and $R^4$ are not simultaneously hydrogen; and pharmaceutically acceptable salts and hydrates thereof.

In one embodiment, $R^1$ is $C_1$-$C_{12}$ aliphatic; which can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl; and $R^4$ is hydrogen.

In another embodiment, $R^4$ is $C_1$-$C_{12}$ aliphatic; which can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl; and $R^1$ is hydrogen.

In another embodiment, $R^1$ is $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl; and $R^4$ is hydrogen.

In a still further embodiment, $R^4$ is $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl; and $R^1$ is hydrogen.

In some embodiments, $R^1$ and $R^4$ are independently $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl.

$R^1$ may be selected from the group consisting of methyl, ethyl, propyl, isopropyl, butyl, isobutyl, sec-butyl, pentyl, hexyl, heptyl and octyl.

In one embodiment $R^1$ is selected from the group consisting of methyl, ethyl, propyl, isopropyl, butyl, isobutyl, sec-butyl, pentyl, hexyl, heptyl and octyl and $R^4$ is hydrogen.

$R^4$ may be selected from the group consisting of methyl, ethyl, propyl, isopropyl, butyl, isobutyl, sec-butyl, pentyl, hexyl, heptyl and octyl.

In some embodiments $R^4$ is selected from the group consisting of methyl, ethyl, propyl, isopropyl, butyl, isobutyl, sec-butyl, pentyl, hexyl, heptyl and octyl and $R^1$ is hydrogen.

In other embodiments $R^1$ and $R^4$ are independently selected from the group consisting of methyl, ethyl, propyl, isopropyl, butyl, isobutyl, sec-butyl, pentyl, hexyl, heptyl and octyl.

$R^3$ may be selected from the group consisting of hydrogen or hydroxyl.

In some embodiments, $R^3$ is selected from the group consisting of hydrogen or hydroxyl; $R^1$ is selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl; and $R^4$ is hydrogen.

In other embodiments $R^3$ is selected from the group consisting of hydrogen or hydroxyl; $R^4$ is selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl; and $R^1$ is hydrogen.

In still further embodiments, $R^3$ is selected from the group consisting of hydrogen or hydroxyl; and $R^1$ and $R^4$ are independently selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl.

In one embodiment, $R^3$ is selected from the group consisting of hydrogen or hydroxyl; $R^1$ is selected from the group consisting of methyl, ethyl, propyl, isopropyl, butyl, isobutyl, sec-butyl, pentyl, hexyl, heptyl and octyl; and $R^4$ is hydrogen.

In another embodiment $R^3$ is selected from the group consisting of hydrogen or hydroxyl; $R^4$ is selected from the group consisting of methyl, ethyl, propyl, isopropyl, butyl, isobutyl, sec-butyl, pentyl, hexyl, heptyl and octyl; and $R^1$ is hydrogen.

In a still further embodiment $R^3$ is selected from the group consisting of hydrogen or hydroxyl; and $R^1$ and $R^4$ are independently selected from the group consisting of methyl, ethyl, propyl, isopropyl, butyl, isobutyl, sec-butyl, pentyl, hexyl, heptyl and octyl.

In one aspect the present invention provides compounds having the formula:

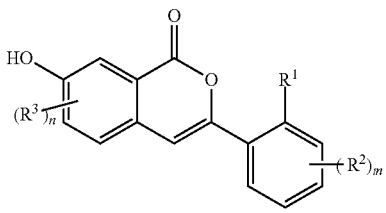

wherein n is 0 to 3; m is 0 to 3;

$R^1$ is selected from the group consisting of $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;

wherein $R^1$ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl;

$R^2$ is independently selected from the group consisting of hydrogen, a hydroxyl, an amino group, a halogen, a cyano group, a nitro group, a nitroso group, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic, $C_1$-$C_{12}$ alkoxy;

$R^3$ is independently selected from the group consisting of hydrogen, a hydroxyl, an amino group, a halogen, a cyano group, a nitro group, a nitroso group, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;

wherein, independently any $R^2$ or $R^3$ can be unsubstituted, or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;

and pharmaceutically acceptable salts and hydrates thereof.

In one embodiment, the present invention provides a compound having the formula:

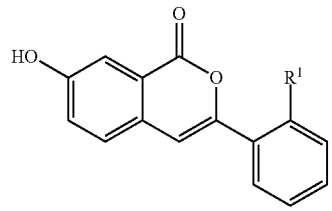

wherein, $R^1$ is selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;

and pharmaceutically acceptable salts and hydrates thereof.

In one embodiment, $R^1$ is $C_{1-12}$ alkyl; which can be unsubstituted or substituted with at least one of a fluorine, chlorine, bromine, iodine Suitably, $R^1$ is selected from the group consisting of methyl, ethyl, propyl, butyl, pentyl, hexyl, isopropyl, —$CFH_2$, —$CF_2H$, —$CF_3$, —$CH_2CF_3$.

Suitably, the compounds of the invention may be selected from the group consisting of:

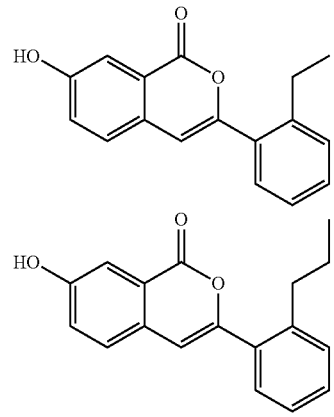

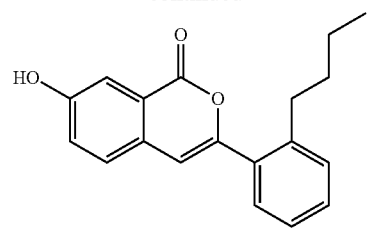
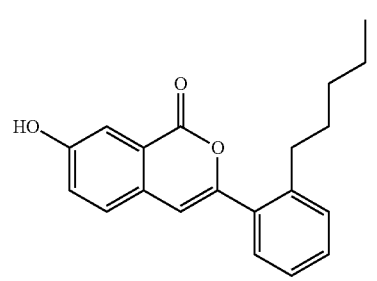
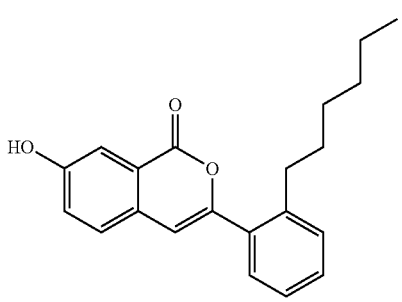
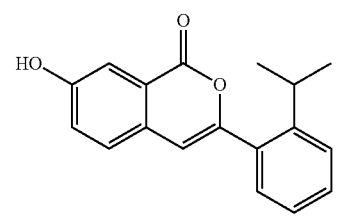
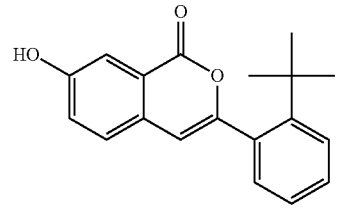
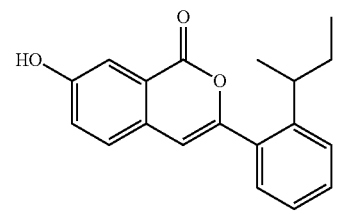
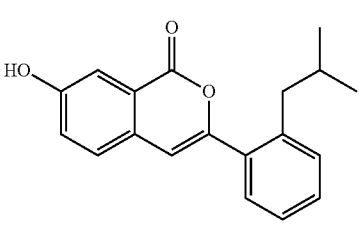
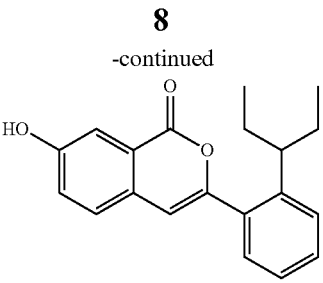
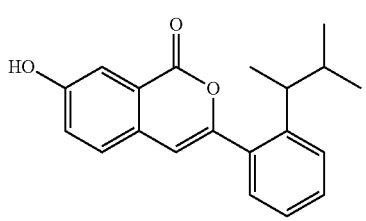
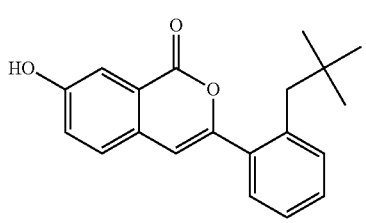
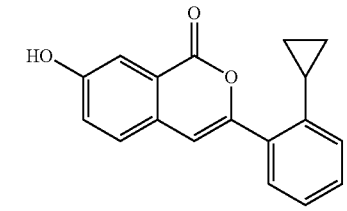
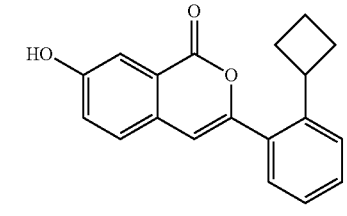
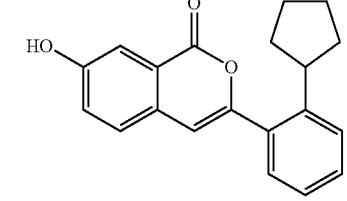
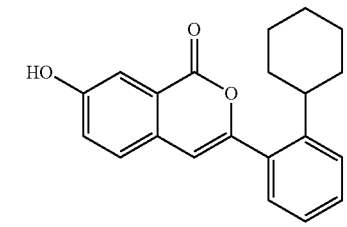
and pharmaceutically acceptable salts and hydrates thereof.
Suitably, the compound can be selected from the group consisting of:

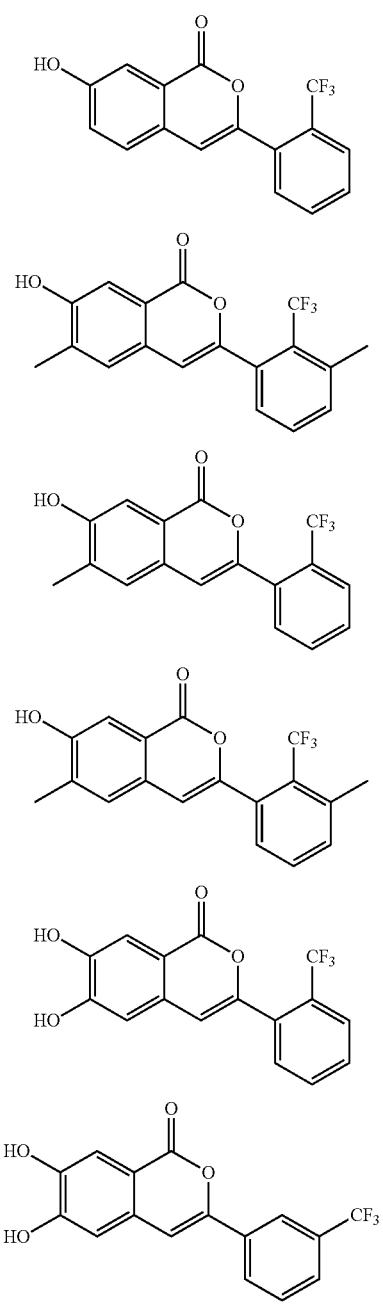

and pharmaceutically acceptable salts and hydrates thereof.

Alternatively, the compound can be selected from the group consisting of:

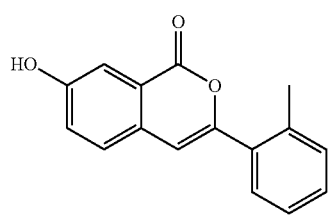 [SMILES: Cc1ccccc1-c1cc2ccc(O)cc2c(=O)o1]

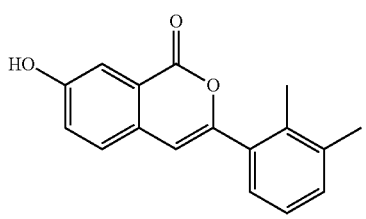

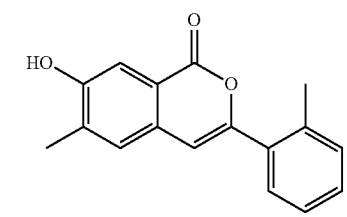

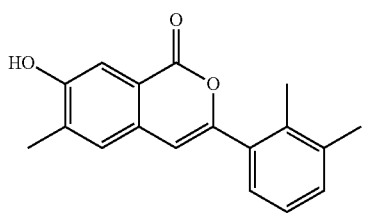

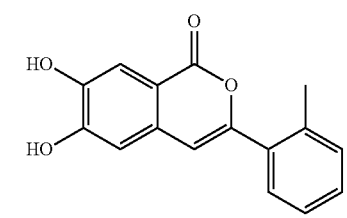

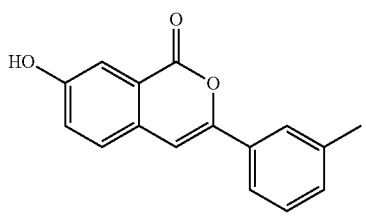

and pharmaceutically acceptable salts and hydrates thereof.

In a preferred embodiment the compound of the invention has the formula:

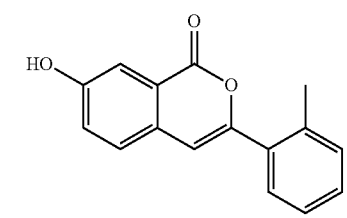

and pharmaceutically acceptable salts and hydrates thereof.

In a further aspect, the present invention provides compounds having the formula

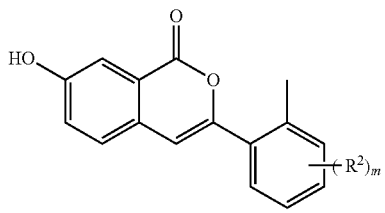

wherein m is 0 to 3;
any R² is independently selected from the group consisting of hydrogen, a hydroxyl, an amino group, a halogen, a cyano group, a nitro group, a nitroso group, $C_1$-$C_6$ aliphatic, $C_1$-$C_6$ alkoxy; wherein R² can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein any R' is independently selected, for each occurrence, from the group consisting of hydrogen and $C_1$-$C_6$ alkyl;
and pharmaceutically acceptable salts and hydrates thereof.

R² can be independently selected from the group consisting of a halogen, a hydroxyl, an amino group, $C_1$-$C_6$ alkyl and $C_1$-$C_6$ alkoxy; and R² can be unsubstituted or substituted with a halogen, for example fluorine.

For example, R² may be a halogen selected from the group consisting of fluorine, chlorine, bromine and iodine. R² may be a $C_1$-$C_6$ alkyl substituted with a halogen selected from the group consisting of fluorine, chlorine, bromine and iodine. For example R₂ may be a CF₃ group, a CH₂F group, a CHF₂ group or a CF₂CF₃ group. R² may be selected from the group consisting of methyl, ethyl, propyl, butyl, pentyl, hexyl, isopropyl, tert-butyl, sec-butyl and isobutyl. R² may be a $C_1$-$C_6$ alkoxy group substituted with a halogen selected from the group consisting of fluorine, chlorine, bromine and iodine. R² may be a methoxy group, an ethoxy group, a propyloxy group, a butyloxy group, a pentyloxy group or a hexyloxy group.

In another aspect the present invention provides compound having the formula

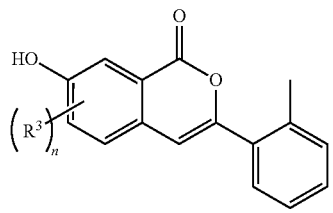

n is 0 to 3;
wherein any R³ is independently selected from the group consisting of hydrogen, a hydroxyl, an amino group, a halogen, a cyano group, a nitro group, a nitroso group, and $C_1$-$C_{12}$ aliphatic; wherein any R³ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;
and pharmaceutically acceptable salts and hydrates thereof.

Any R³ is independently selected from the group consisting of hydrogen, a halogen, a hydroxyl, an amino group and $C_1$-$C_6$ alkyl; and R³ can be unsubstituted or substituted with a halogen, for example fluorine.

In some embodiments R³ is a hydroxyl, R¹ is $C_1$-$C_{12}$ alkyl and R⁴ is hydrogen.

In another aspect the present invention provides compounds having the formula

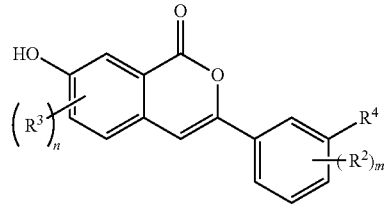

wherein n is 0 to 3; m is 0 to 3;
R² is independently selected from the group consisting of hydrogen, a hydroxyl, an amino group, a halogen, a cyano group, a nitro group, a nitroso group,
$C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic, $C_1$-$C_{12}$ alkoxy;
R³ is independently selected from the group consisting of hydrogen, a hydroxyl, an amino group, a halogen, a cyano group, a nitro group, a nitroso group,
$C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;
wherein, independently any R² or R³ can be unsubstituted, or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;
R⁴ is selected from the group consisting of $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;
wherein R⁴ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl; and pharmaceutically acceptable salts and hydrates thereof.

In some embodiments $R^3$ is hydroxyl.

In some embodiments $R^3$ is a hydroxyl, $R^4$ is $C_1$-$C_{12}$ alkyl and $R^1$ is hydrogen.

In some embodiments $R^3$ is a hydroxyl in the 6-position of the isocoumarin ring.

n can be 0, 1, 2 or 3.

In some embodiments n is 0. In other embodiments n is 1 or 2 or 3.

m can be 0, 1, 2 or 3.

In some embodiments m is 0. In other embodiments m is 1 or 2 or 3.

In some embodiments n and m are 0.

In another aspect the present invention provides a compound having the formula

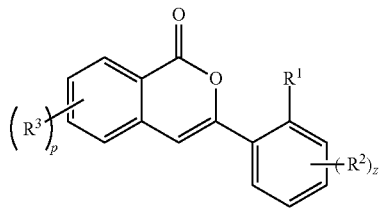

wherein p is 0 to 4; z is 0 to 4;

$R^1$ is selected from the group consisting of $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;

wherein $R^1$ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;

$R^2$ is independently selected from the group consisting of hydrogen, a hydroxyl, an amino group, a halogen, a cyano group, a nitro group, a nitroso group, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic, $C_1$-$C_{12}$ alkoxy;

$R^3$ is independently selected from the group consisting of hydrogen, a hydroxyl, an amino group, a halogen, a cyano group, a nitro group, a nitroso group, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ hetero aromatic;

wherein independently any $R^2$ or $R^3$ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl;

for use in the treatment of cancer.

p can be 0, 1, 2, 3 or 4. z can be 0, 1, 2, 3 or 4.

In some embodiments p is 0. In other embodiments p is 1, 2, 3 or 4.

In some embodiments p is 0 and $R^1$ is selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl.

In other embodiments p is 0 and $R^1$ is selected from the group consisting of methyl, ethyl, propyl, isopropyl, butyl, isobutyl, sec-butyl, pentyl, hexyl, heptyl and octyl.

In one embodiment p is 0 and $R^1$ is methyl.

MIF is overexpressed in numerous cancers including lung cancer, ovarian cancer, breast cancer, hepatocellular cancer, oesophageal squamous-cell cancer, bladder cancer, cervical squamous-cell cancer, pancreatic cancer, glioblastomas, prostate cancer, osteosarcoma, colorectal cancer, head and neck cancer and malignant melanoma, gastric cancer, glioma, nasopharyngeal cancer.

Suitably, the compounds of the invention may be used in the treatment of a cancer selected from the group consisting of: lung cancer, ovarian cancer, breast cancer, hepatocellular cancer, oesophageal squamous-cell cancer, bladder cancer, cervical squamous-cell cancer, pancreatic cancer, glioblastomas, prostate cancer, osteosarcoma, colorectal cancer, head and neck cancer and malignant melanoma, gastric cancer, glioma, nasopharyngeal cancer.

In one aspect the present invention provides compounds having the formula:

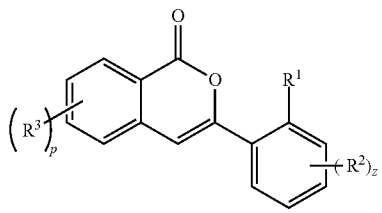

wherein p is 0 to 4; z is 0 to 4;

$R^1$ is selected from the group consisting of hydrogen, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;

wherein $R^1$ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;

$R^2$ is independently selected from the group consisting of hydrogen, a hydroxyl, an amino group, a halogen, a cyano group, a nitro group, a nitroso group,
$C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic, $C_1$-$C_{12}$ alkoxy;

$R^3$ is independently selected from the group consisting of hydrogen, a hydroxyl, an amino group, a halogen, a cyano group, a nitro group, a nitroso group,
$C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;
wherein independently any $R^2$ or $R^3$ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl;
wherein when p is 0, $R^1$ is not hydrogen;
for use in the treatment of a cancer selected from the group consisting of: lung cancer, ovarian cancer, breast cancer, hepatocellular cancer, oesophageal squamous-cell cancer, bladder cancer, cervical squamous-cell cancer, pancreatic cancer, glioblastomas, prostate cancer, osteosarcoma, colorectal cancer, head and neck cancer and malignant melanoma, gastric cancer, glioma, nasopharyngeal cancer.

Suitably, the compounds of the invention are used in the treatment of lung cancer.

In one aspect the present invention provides a compound having the formula:

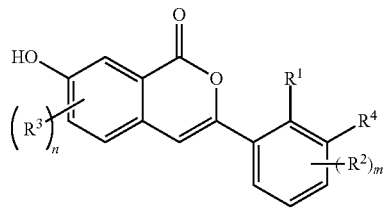

wherein n is 0 to 3; m is 0 to 3;
$R^1$ and $R^4$ are the same or different and are independently selected from the group consisting of hydrogen, $C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;
wherein $R^1$ and $R^4$ can independently be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein each R' is independently selected, from the group consisting of hydrogen and $C_1$-$C_6$ alkyl;

$R^2$ is independently selected from the group consisting of hydrogen, a hydroxyl, an amino group, a halogen, a cyano group, a nitro group, a nitroso group,
$C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic, $C_1$-$C_6$ alkoxy;

$R^3$ is independently selected from the group consisting of hydrogen, a hydroxyl, an amino group, a halogen, a cyano group, a nitro group, a nitroso group,
$C_1$-$C_{12}$ aliphatic, $C_3$-$C_{10}$ cycloaliphatic, $C_2$-$C_{10}$ aliphatic heterocycle, $C_6$-$C_{20}$ aromatic and $C_2$-$C_{20}$ heteroaromatic;
wherein, independently any $R^2$ or $R^3$ can be unsubstituted, or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;
wherein $R^1$ and $R^4$ are not simultaneously hydrogen;
and pharmaceutically acceptable salts and hydrates thereof;
for use in the treatment of lung cancer.

Suitably, the present invention provides compounds having the formula:

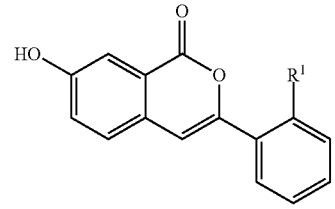

wherein, $R^1$ is selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, oxo, $C_3$-$C_6$ cycloalkyl, $C_3$-$C_6$ heterocyclyl, $C_2$-$C_5$ heteroaryl and $C_6$-$C_{10}$ aryl; wherein R' is independently selected, for each occurrence, from the group consisting of hydrogen and $C_1$-$C_6$ alkyl;
for use in the treatment of lung cancer.
In yet a further aspect the present invention provides compounds selected from the group consisting of:
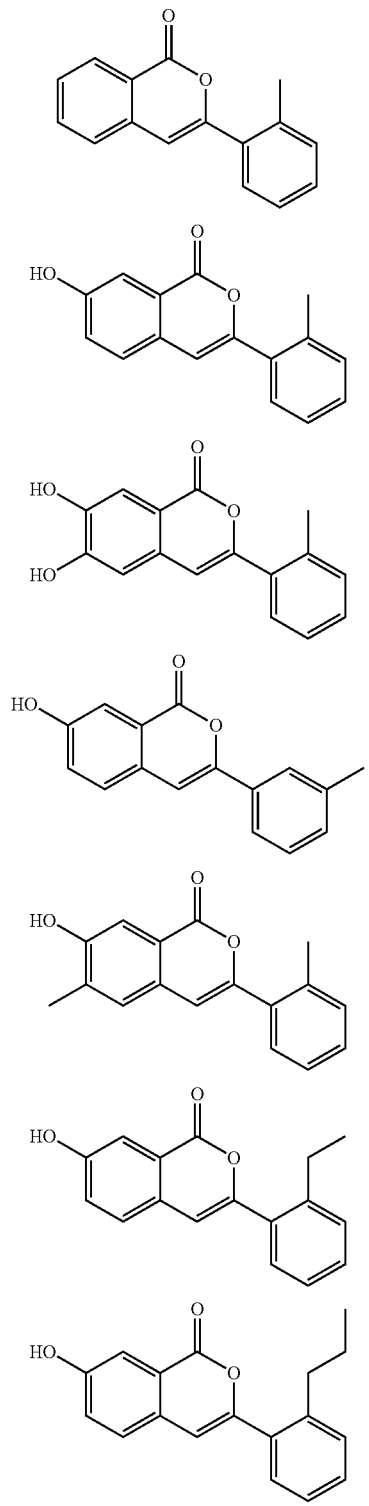
-continued
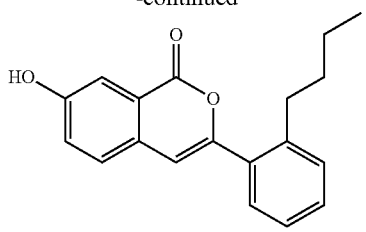
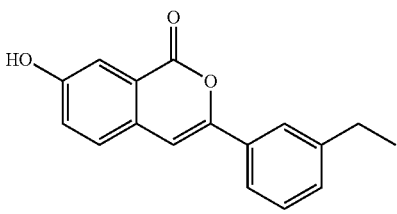
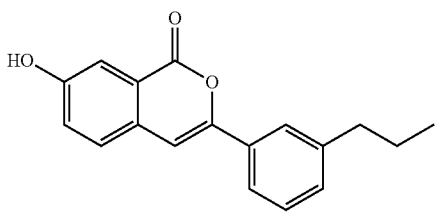
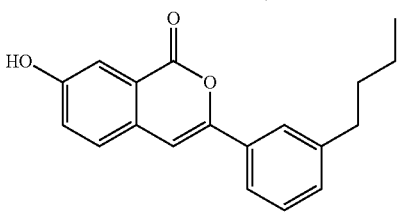
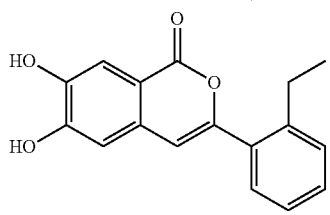
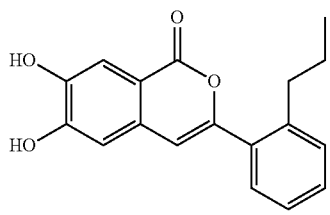
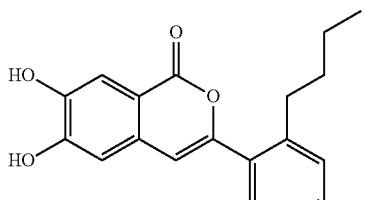
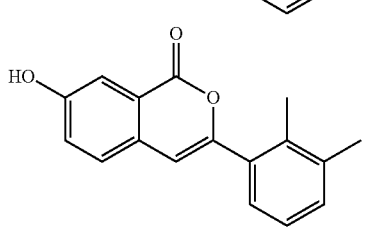

-continued
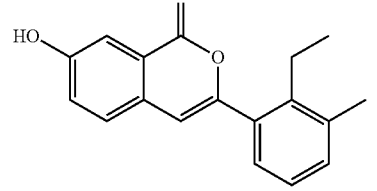
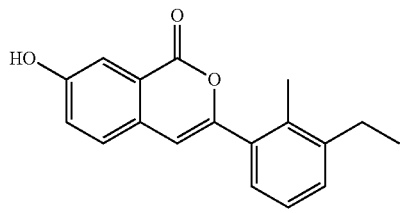
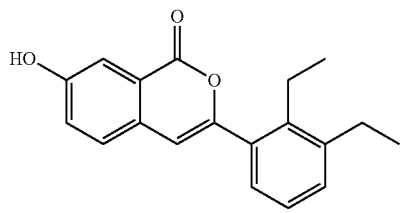
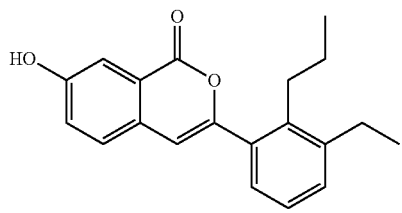
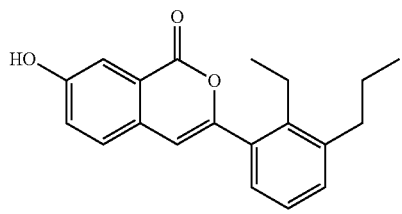
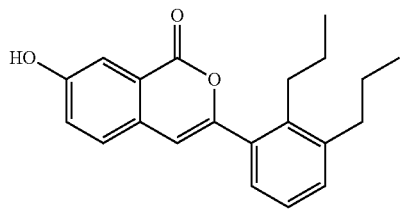
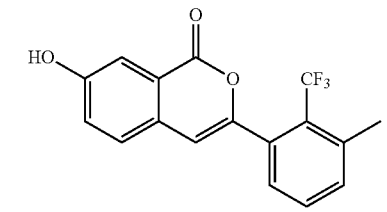
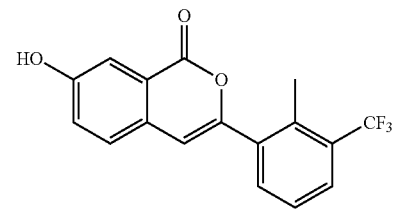
-continued
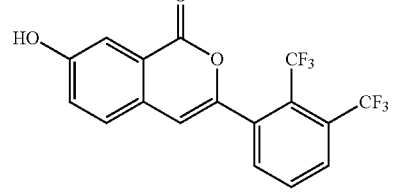
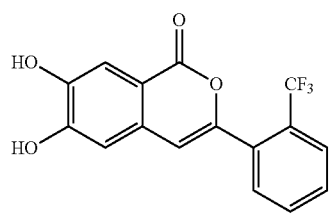
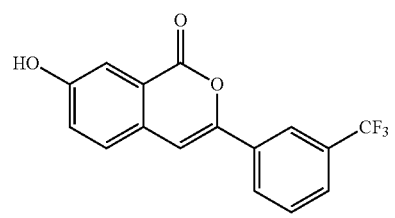
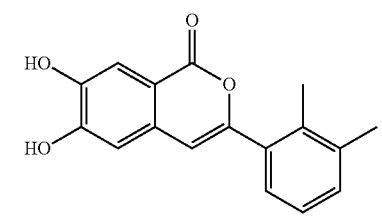
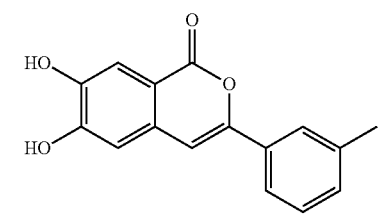
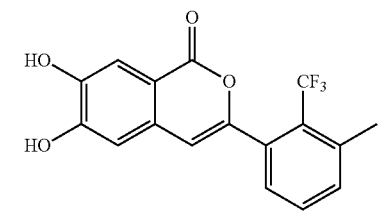
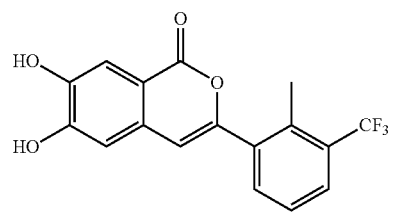
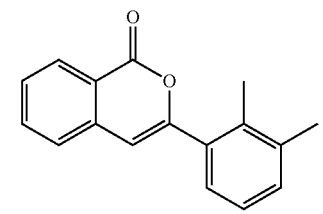

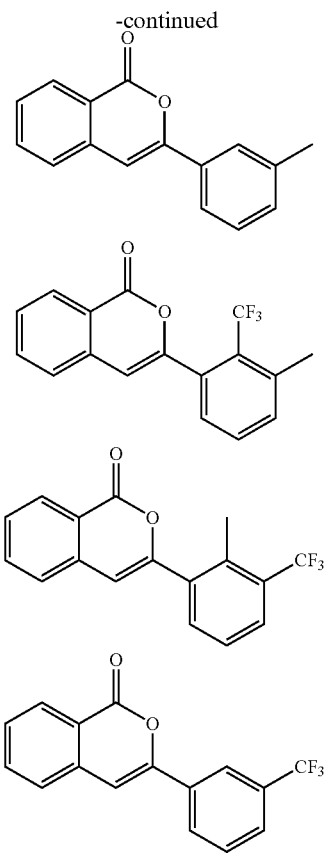

for use in the treatment of cancer.

The cancer may be selected from the group consisting of: lung cancer, ovarian cancer, breast cancer, hepatocellular cancer, oesophageal squamous-cell cancer, bladder cancer, cervical squamous-cell cancer, pancreatic cancer, glioblastomas, prostate cancer, osteosarcoma, colorectal cancer, head and neck cancer and malignant melanoma, gastric cancer, glioma, nasopharyngeal cancer.

Suitably, the compound of the invention are used in the treatment of lung cancer.

In yet a further aspect, the present invention provides a method for treating a disease associated with high MIF expression and/or activity, the method comprising administering to a subject in need thereof, a therapeutically-effective amount of a compound of the invention.

BRIEF DESCRIPTION OF THE DRAWINGS

FIG. 1 shows inhibition of MIF tautomerase enzymatic activity. Inhibition was calculated as the reduction of the rate of change of the tautomerase reaction with the addition of the inhibitor averaged over five minutes.

FIG. 2 shows inhibition of LPS induced TNF-α production. (A) RAW macrophage cells were plated at $1 \times 10^5$ per well and pre-treated with the inhibitors at 100 μM for 30 minutes prior to stimulation with 100 ng/ml LPS. After 16 hours, supernatants were collected and assessed for levels of TNF-α using TNF-α ELISA kit. (B) Raw cells were pre-treated with 50 μM of each inhibitor 30 minutes prior to LPS stimulation and supernatants were assessed after 16 hours for TNF-α level. (C) RAW cells were pre-treated with 10 μM of Tautomerase inhibitors 30 minutes prior to LPS stimulation. Data are presented as mean and SEM (n=6).

FIG. 3 shows inhibition of MIF tautomerase enzymatic activity of 5 chosen compounds. Inhibition seen with 100 ng/ml MIF with its substrate L-dopachrome incubated with each of the inhibitors at 100 μM measured with a spectrophotometer over 20 minutes.

FIG. 4 shows inhibition of MIF induced PGE-2. RAW macrophage cells were plated at a cell density at $1 \times 10^5$ per well and were pre-treated with ISO-1 and TI 19 and then treated with 100 ng/ml of LPS overnight at 37° C. in a humidified 5% $CO_2$ incubator. RAW cells were treated with 100 μM of inhibitors as indicated. Supernatants were assessed using PGE-2 ELISA kit. (p<0.05, p>0.01, Data presented as mean and SEM (n=6)).

FIG. 5 shows inhibition of MIF enzymatic activity reduces cell proliferation. 100 ng/ml of rMIF significantly promotes proliferation of LLC compared to untreated LLC cells. Proliferation is inhibited significantly in the presence of 100 μM of TI 19 but less so in the presence of ISO-1. (***p<0.001, Data presented as mean+SEM, n=6)

FIG. 6 shows Lewis lung cell tumour volume is significantly lower in MIF-KO and MIF-P1G mice compared to wild type. Lewis Lung carcinoma cells ($5 \times 10^5$) were injected sub-cutaneously into the left flank of C57BL/6 WT mice, P1G and MIF KO mice. Caliper measurements were taken twice weekly and tumour volume ($mm^3$) was calculated as $0.5 \times L \times W^2$ (n=4).

FIG. 7 shows the gross appearance of subcutaneous tumours at day 24 of the model. FIG. 7A shows a tumour in an untreated mouse, FIG. 7B is a control and shows a tumour wherein the mouse was treated with 5% DMSO and FIG. 7C shows a tumour wherein the mouse was treated with TI 19.

FIG. 8 shows that inhibition of MIF tautomerase activity attenuates tumour growth. Lewis Lung carcinoma cells ($5 \times 10^5$) were injected sub-cutaneously into the left flank of C57BL/6 mice. Animals were injected intraperitoneally 30 min prior to tumour inoculation and twice weekly thereafter, with 35 mg/kg TI (tautomerase inhibitor solubilized in DMSO) or as indicated. Caliper measurements were taken twice weekly and tumour volume ($mm^3$) was calculated as $0.5 \times L \times W^2$. (**p<0.01, n=4).

FIG. 9 shows that inhibition of MIF tautomerase activity attenuates tumour growth. Lewis Lung carcinoma cells ($5 \times 10^5$) were injected sub-cutaneously into the left flank of C57BL/6 mice. Once the tumour had become palpable on the flank of the mouse (7-8 days after innoculation), the animals were injected intraperitoneally and twice weekly thereafter, with 35 mg/kg TI (tautomerase inhibitor solubilized in DMSO) or as indicated. Caliper measurements were taken twice weekly and tumour volume ($mm^3$) was calculated as $0.5 \times L \times W^2$. (**p<0.01, n=4).

FIG. 10 shows the inhibitory effect of analogues of TI 19 on MIF tautomerase enzymatic activity. Inhibition was calculated as the reduction of the rate of change of the tautomerase reaction with the addition of the inhibitor averaged over five minutes.

FIG. 11 shows the inhibitory effect of analogues of TI 19 on LPS induced TNF-α production. RAW macrophage cells were plated at $1 \times 10^5$ per well and pre-treated with the inhibitors at 100 μM for 30 minutes prior to stimulation with 100 ng/ml LPS. After 16 hours, supernatants were collected and assessed for levels of TNF-α using a TNF-α ELISA kit.

DETAILED DESCRIPTION

The disclosure is based, in part, upon the discovery that certain compounds disclosed herein have the ability to modulate the activity of MIF.

Before further description, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The term "pharmaceutically acceptable carrier" or "pharmaceutically acceptable excipient" as used herein refers to any of the following: solvents, dispersion media, coatings, isotonic and absorption delaying agents, with the proviso that they are compatible with pharmaceutical administration. The use of carriers and excipients for pharmaceutically active substances is well known to those skilled in the art. Furthermore, the compositions may further comprise other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

The compounds contemplated herein can be administered to a mammal, such as a human, but can also be administered to other mammals such as an animal, for example domestic animals, farm animals and laboratory animals, in need of veterinary treatment. The mammal treated in the methods contemplated herein is suitably a mammal with cancer.

As used herein, the term "therapeutically effective amount" refers to the amount of the compound in question that will elicit the desired biological or medical response in a tissue, system or animal (e.g., mammal or human). The compounds contemplated herein are administered to the "subject", "individual" or "patient", (which can be a mammal as described above), in therapeutically effective amounts to treat a disease or disorder. Alternatively, a therapeutically effective amount of a compound is the quantity required to achieve a desired therapeutic and/or prophylactic effect.

The term "pharmaceutically acceptable salt(s)" as used in this specification refers to salts of acidic or basic groups that may be present in compounds used in the compositions. Basic compounds of the contemplated herein are capable of forming a plethora of salts with various inorganic and organic acids. Pharmaceutically acceptable acid addition salts of such basic compounds are those that form non-toxic acid addition salts, i.e., salts containing pharmacologically acceptable anions, including, but not limited to any of the following: chloride, bromide, iodide, nitrate, sulfate, bisulfate, methanesulfonate, ethanesulfonate, benzenesulfonate, p-toluenesulfonate, phosphate, acid phosphate, malate, oxalate, nicotinate, isonicotinate, acetate, lactate, salicylate, citrate, tartrate, oleate, tannate, pantothenate, saccharate, formate, benzoate, bitartrate, ascorbate, succinate, maleate, gentisinate, fumarate, gluconate, glucaronate, glutamate, and pamoate (i.e., 1,1'-methylene-bis-(2-hydroxy-3-naphthoate)) salts.

Acidic compounds contemplated herein are capable of forming a plethora of pharmaceutically acceptable salts with various basic substances. For example, the pharmaceutically acceptable salts may include alkali metal or alkaline earth metal salts and, particularly, calcium, magnesium, sodium, lithium, zinc, potassium, and iron salts. Compounds comprising a basic or acidic moiety may also form pharmaceutically acceptable salts with amino acids. The compounds of the disclosure may contain both acidic and basic groups; for example, one amino and one carboxylic acid group. In such a case, the compound can exist as an acid addition salt, a zwitterion, or a base salt.

The term "stereoisomers" when used herein consist of all enantiomers or diastereomers. These compounds may be designated by the symbols "(+)," "(−)," "R" or "S," depending on the configuration of substituents around the stereogenic carbon atom in question. The person having ordinary skill in the art will recognize that a structure may denote a chiral center implicitly.

The compounds disclosed herein can exist in solvated as well as unsolvated forms, for example as hydrates or with other pharmaceutically acceptable solvents such ethanol, and the like. The compounds disclosed herein embrace both solvated and unsolvated forms. The compound of the invention can be amorphous. The compound of the invention can exist as a single polymorph or as a mixture of polymorphs. In some embodiments, the compound of the invention is in a crystalline form.

The disclosure also embraces isotopically labeled compounds of the disclosure, wherein said isotopically labelled compounds are identical to the compounds of the invention except that one or more atoms are replaced by an isotopic variant. Isotopes that can be incorporated into compounds of the disclosure include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more hydrogen atoms replaced with deuterium.

The term "prodrug" as used herein refers to compounds that are transformed in vivo to yield a disclosed compound or a pharmaceutically acceptable salt, hydrate or solvate of the compound. The prodrug may be transformed in vivo through various mechanisms for example, through the action of esterase, amidase or phosphatase enzymes, or via oxidative and or reductive metabolism. Such a transformation releasing the drug from the prodrug could occur in various locations, for example, in the intestinal lumen or upon transit of the intestine, blood or liver. The transformation may also or alternatively be by, chemical hydrolysis or enzymatic attack. Prodrugs are well known to those skilled in the art. For example, if a compound of the invention or a pharmaceutically acceptable salt, hydrate or solvate of the compound contains a carboxylic acid group, a prodrug may comprise an ester formed by the replacement of the hydrogen atom of the acid group with a group such as ($C_{1}$-$C_{8}$) alkyl, ($C_{2}$-$C_{12}$) alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$) alkyl (such as β-dimethylamino ethyl), carbamoyl-($C_{1-2}$) alkyl, N,N-di($C_{1-2}$)alkylcarbamoyl-($C_{1-2}$)alkyl and piperidino-, pyrrolidino- or morpholino($C_{2-3}$)alkyl.

Similarly, if a compound contemplated herein contains an alcohol functional group, a prodrug can be formed by the replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl ($C_{1-6}$) alkoxycarbonyloxymethyl, N—(C1-6)alkoxycarbonylaminomethyl, succinoyl, ($C_{1-6}$)alkanoyl, α-amino($C_{1-4}$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O(C$_{1-6}$)alkyl)$_2$ or glycosyl (the radical resulting from the removal of a hydroxyl group of the hemiacetal form of a carbohydrate).

If a compound contemplated herein incorporates an amine functional group, a prodrug can be formed, for example, by creation of an amide or carbamate, an N-acyloxyakyl derivative, an (oxodioxolenyl)methyl derivative, an N-Mannich base, imine or enamine.

MIF Inhibitors
Docking Studies

In order to identify potential inhibitors of MIF an in silico screen of a virtual library of compounds was initially performed, wherein the compounds were docked into the active site of MIF tautomerase.

The crystal structure of MIF co-crystallized with the substrate p-hydroxyphenylpyruvate (HPP) was downloaded from the Protein Data Bank (PDB code 1CA7). The protein was prepared using the automatic protein preparation protocol in Molecular Operating Environment (MOE) software (Chemical Computing Group).

Due to its speed and accuracy, the docking program Fast Rigid Exhaustive Docking (FRED) was chosen to conduct a virtual screening campaign. FRED (OpenEye Scientific Software) is a protein-ligand docking program, which takes a multi-conformer library/database and receptor file as input and outputs molecules of the input database most likely to bind to the receptor.

Chemgauss is a scoring function developed by OpenEye, which uses Gaussian functions to describe the shape and chemistry of molecules. FRED's docking strategy is to exhaustively score all possible positions of each ligand in the active site. The exhaustive search is based on rigid rotations and translations of each conformer. This novel strategy completely avoids the sampling issues associated with stochastic methods used by many other docking programs.

In order to validate our model, the ability of FRED to reproduce the bioactive conformation of a number of ligands was assessed. 50, 100 and 500 conformers of the HPP ligand as well as the prototypical MIF inhibitor ISO-1 were generated using OMEGA (OpenEye) and docked into the MIF active site. An evaluation of the various scoring functions provided by FRED showed that the Chemgauss3 scoring function was consistently the most accurate and ranked the bioactive conformation first out of the conformational data set docked. Thus, Chemgauss3 became the preferred scoring function throughout the rest of the virtual screening campaign.

Further validation was then carried out on the model using a virtual haystack followed by receiver operating characteristic curve (ROC curve) analysis. A data set consisting of 40 known active MIF inhibitors downloaded from BindingDB (www.BindingBD.org) were combined with a set containing 960 'presumed' inactive compounds obtained from the Maybridge hit finder database. 50, 100 and 500 conformers of this data set were generated using OMEGA to see if the number of conformers had an effect on the enrichment rate.

The virtual haystack was then docked using FRED's Chemgauss3 scoring function. Receiver operating characteristic curves (ROC) were then generated to establish the ability of the model to distinguish between the active compounds and the inactive or decoy compounds. In this case the AUC (area under the curve) was 0.87 (the maximum value is 1.0, therefore 0.87 is rated a very good ROC curve suggesting the model is accurately able to distinguish between active compounds and inactive ones) for the 50 conformer dataset (differences in this number were not seen for the 100 and 500 conformers).

A vendor dataset consisting of roughly 205000 molecules was downloaded from www.SPECS.net. The set was cleaned and prepared using the prepare ligands protocol on Pipeline Pilot. The dataset was further streamlined through a filtering protocol, which filtered the compounds for 'known MIF inhibitor like physiocochemical properties'. 50 conformers of this dataset were then generated using OMEGA and docked into the MIF active site with FRED. Results were then clustered into 25 clusters, the compounds were then inspected manually and a subset was chosen for testing. 25 potential MIF inhibitors were selected for biological assessment.

Materials and Methods
Cell Culture
RAW 264.7

The RAW 264.7 cell line was obtained from the ECACC, catalogue number 85062803. RAW cells were maintained in DMEM medium (Gibco—cat no. 41965-039) supplemented with 10% FCS (Gibco—cat no. 10270-106), 100 U/ml penicillin and streptomycin (Gibco—cat no. 15070-063) and 2 mM L-Glutamine (Gibco—cat no. 25030-081). Cells were maintained in a humidified atmosphere containing 5% CO$_2$ at 37° C. Cells were passaged every 2-3 days when they reached 80-90% confluency. Cells were removed from bottom of flasks using cell scrapers and centrifuged for 5 minutes at room temperature at 400 g on a bench top centrifuge. Medium was discarded and cells were re-suspended in fresh DMEM medium.

Lewis Lung Carcinoma (LLC1)

The LLC1 cell line was obtained from Prof. Tariq Sethi (Kings College London). LLC1 are a Lewis Lung carcinoma cell line expressing stably transfected *Gaussia luciferase*. LLC1 cells were maintained in DMEM supplemented with 10% FCS, 2 mM L-glutamine and 100 U/ml penicillin/streptomycin. Cells were subcultured by removing medium and adding 5 ml of 0.05% Trypsin-EDTA (Gibco—cat no. 25200-056) for 1 minute at 37° C. Trypsin was neutralised by adding medium. The cells were collected and spun for 5 minutes in a bench top centrifuge and resuspended in fresh medium. Cells were passaged every 2-3 days.

Cell Conditions

All cells were maintained in sterile environment at 37° C. in humidified and concentrated CO$_2$ (5%) atmosphere. All cells were subcultured when they reached 80-90% confluency.

Generation of Recombinant MIF

Human recombinant MIF was purified as per Bernhagen et al. (Biochemistry, 1994. 33(47): p. 14144-55). Briefly, BL21 *E. coli* cells expressing the pET11b-MIF construct were grown to an absorbance at 600 nm (OD) of 0.6-0.08. Isopropyl 1-thio-P-D-galactopyranoside (IPTG) (Sigma—cat no. 16758) was added to a final concentration of 1 mM to induce expression of the MIF gene and incubated for another 3 hours. Bacteria were then harvested by centrifugation and the cell pellets were then frozen. Protein purification was then out sourced to Scottish Biomedical, where the bacterial pellets were thawed and resuspended in 3 ml of Tris-buffered saline. The bacteria were then lysed by adding an equivalent number of glass beads and vortexing strongly for 10 minutes. Glass beads were removed by centrifugation at 1000 g for 10 minutes and the bacterial extract was centrifuged at 1000 g for a further 30 minutes. The supernatant was then sterile-filtered through a 45 ppm and then 22 ppm membrane filter and put through a MONO Q anion exchange chromatography column. MIF was eluted using Tris-buffered saline in the first flow-through fractions and pooled and placed on ice. These pooled fractions were then applied to a $C_8$-SepPak reverse phase column. Unbound material was eluted by washing with water and 20% acetonitrile/water. MIF was then eluted using 6 column volumes of 60% acetonitrile/water. This sample was then renatured by dissolving MIF at a concentration of 200-400 pg/ml in 20 mM sodium phosphate buffer containing 8M urea and 5 mM DTT and dialysed against 20 mM sodium phosphate buffer.

MIF Regulation of TNF-α

RAW 264.7 macrophage cells were plated at $1 \times 10^5$/ml in 450 μl of medium in a 48 well plate. 16 hours later cells were treated with ISO-1 or Tautomerase Inhibitors at a final concentration of 10, 50 or 100 μM for 30 minutes before stimulation with 100 ng/ml LPS. Supernatants were collected after 20 hours for determination of TNF-α levels. TNF-α levels were determined using a TNF-α specific ELISA (CAT # DY410 R&D Syst).

TNF-α ELISA 96 well plates were coated with 50 μl of Capture Antibody (0.8 m/ml) in PBS and sealed and incubated overnight at 4° C. Plates were then washed three times in 0.05% PBS Tween and plates blotted. Plates were blocked by adding 150 μl of 1% BSA in PBS (Gibco—cat no. 14190-094) to each well and incubated at room temperature for 2 hours. Plates were washed again as previously described. 50 μl of sample or standard was added to each well and incubated for overnight at 4° C. Plates were then washed again as described. 50 μl of the detection Antibody (200 ng/ml) in 1% BSA in PBS was added to each well and incubated for 2 hours at room temperature. Plates were then washed again as described. 50 μl of working concentration of Streptavidin—HRP was added to each well and plates were covered and incubated for 20 minutes at room temperature. 50 μl of substrate solution (One OPD tablet and one urea hydrogen peroxide/buffer tablet were dissolved in 20 ml of water to yield a ready to use buffered solution, Sigma—cat no. 9187-50) was added to each well and incubated for 20 minutes at room temperature. 25 μl of 2N $H_2SO_4$ was added to each well to stop the reaction. The optical density of each well was then measured with a spectrophotometer at 450 nm.

PGE-2 ELISA

Raw macrophage murine cells were plated at a cell density of $1 \times 10^5$ and pre-treated with 100 μM of each of the inhibitors at concentration of 100, 50 or 10 μM for 30 minutes at 37° C. in a humidified 5% $CO_2$ incubator. Raw macrophage cells were then treated with 100 ng/ml of LPS and supernatants were collected after 16 hours at 37° C. in a humidified 5% $CO_2$ incubator and analysed for PGE-2 production. Levels of PGE-2 were measured by ELISA. (CAT # KGE004 R&D Syst).

LLC-GLuc Proliferation Assays with rMIF

LLC-GLuc cells were plated in a 6 well plate at a density of $5 \times 10^4$ cells/ml in DMEM supplemented with P/S, 10% FCS and L-Glu. After overnight adherence, 100 ng/ml MIF was added along with the inhibitors or DMSO to a total of 1 ml serum free medium. Cells were harvested after 48 hours by trypsinisation and counted in a haemocytometer.

Subcutaneous LLC1 Model

Log phase cultures of LLC-1 cells were harvested by trypsinisation and washed three times with sterile phosphate buffered saline (PBS) and resuspended at a cell density of $5 \times 10^5$/ml in PBS. Animals were shaved with an electric shaver 24 hours before subcutaneous injection. $5 \times 10^5$ Lewis Lung cells were injected subcutaneously into the left flank of C57BL/6 mice of 6-8 weeks. Animals were monitored for the duration of the experiment and tumour measurements were recorded twice weekly with a digital callipers. Tumour volume ($mm^3$) was calculated as $0.5 \times L \times W^2$, where length is representative of the larger tumour diameter and the width represents the smaller tumour diameter. Animals are sacrificed when tumours reach a diameter of 15 mm or if tumours become ulcerated. Tumours are then removed along with the lungs, spleen and liver.

Lung carcinoma cells ($5 \times 10^5$) were injected sub-cutaneously into the left flank of C57BL/6 WT mice, C57BL/6 MIF KO mice or C57BL/6 P1G mice. Caliper measurements were taken twice weekly and tumour volume ($mm^3$) was calculated as $0.5 \times L \times W^2$.

In Vivo Tautomerase Inhibitor Treatment 30 minutes prior to LLC-1 inoculation, inhibitors (TI 19/ISO-1) were administered at a concentration of 35 mg/kg in a volume of 100 μl 5% DMSO in sterile PBS. Control groups were given injections of vehicle 5% DMSO in sterile PBS or sterile PBS alone. Animals were treated twice weekly for four weeks.

Biological Assays

Assays for Assessment of Small Molecule Inhibitors of MIF

Tautomerase Inhibition Assay

MIF has been shown to possess a unique enzymatic activity, it catalyses the conversion of L-dopachrome into its indole derivative, dihydroxyindole carboxylic acid. The ability of candidate compounds to inhibit the tautomerase activity of MIF is quantitated using hydroxyphenyl pyruvic acid (HPP) as a substrate.

L-dopachrome methyl ester was prepared at 2.4 mM through oxidation of L-3,4-dihydroxyphenylalanine methyl ester with sodium periodate. The solution was mixed well and placed at room temperature for 5 minutes before being placed on ice in the dark. 100 ng of rMIF was added to each of the Tautomerase Inhibitors or ISO-1 at a number of concentrations (1, 50 and 100 μM) with substrate. The decrease in absorbance was measured with a spectrophotometer at 475 nm every 10 seconds for 10 minutes.

The rate of the reaction of rMIF and substrate alone was measured over time at 475 nm. This was compared to the rate of this reaction with the addition of 100 μM of each of the inhibitors. Inhibition was calculated as the percentage in the reduction of the rate of change with the addition of the inhibitor averaged over five minutes.

Each of the 25 potential tautomerase inhibitors were analysed in this tautomerase assay. This allowed us to determine how effective each of the inhibitors was at specifically reducing the enzymatic activity of MIF. FIG. 1 shows each of the compounds in this tautomerase assay.

Of the compounds tested compounds TI 1, 2, 4, 7, 8, 11, 14, 19, 20, 21 & 23 reduced tautomerase activity by over 70%. As can be seen in FIG. 1, 18 of the panel of potential MIF inhibitors were more effective than the commercially available tautomerase inhibitor ISO-1. TI 19, one of the smaller compounds in the panel was seen to have one of the better reductions of MIF enzymatic activity, with a 74% reduction in colour change seen.

FIG. 3 shows the inhibition of MIF tautomerase enzymatic activity for 5 exemplary compounds. TI 19 demonstrated the highest percentage inhibition of MIF enzymatic activity.

Effect of Compounds on the Production of TNF-α

Macrophage migration inhibitory factor was originally thought to target the migration of macrophages, therefore giving it its name; however macrophages have since been found to be one of the main sources of MIF released after toxic shock. MIF has been reported as an important regulator of responses to Gram-negative bacteria in-vitro and in vivo.

Furthermore, monocytes/macrophages and activated T cells which play a key role in the inflammatory response in the pathogenesis of several diseases states including auto-immune and inflammatory diseases are known to secret MIF. In addition, the production of proinflammatory mediators such as tumour necrosis factor-α (TNF-α), interleukin (IL)-1β, IL-6 and IL-8, each of which functions in the induction of the proinflammatory response, has been shown to be stimulated by MIF.

Macrophages are an essential source of MIF. RAW 264.7 is a mouse leukemic monocyte macrophage cell line. Pre-formed MIF protein as well as MIF mRNA is found in non-stimulated RAW 264.7 cells. MIF is secreted upon stimulation of these cells with very low concentrations of LPS.

The MIF inhibitor ISO-1 has the ability to reduce circulating levels of TNF-α in an LPS induced model of murine sepsis. The role of MIF in this cellular response can be exploited to screen inhibitors of the enzymatic activity of MIF. Using the RAW 264.7 cell line, ISO-1 has been shown to inhibit TNF-α production induced by addition of LPS.

Initially the panel of 25 novel potential tautomerase inhibitors was screened in an in-vitro system. In order to do this we exploited the fact that MIF is needed for optimal LPS induced TNF-α production. We therefore reasoned that our potential TIs should be able to inhibit LPS induced TNF-α in RAW macrophage murine cells. RAW macrophage murine cells were plated at 37° C. in a humidified 5% $CO_2$ incubator. 16 hours later the cells were pre-treated with each of the inhibitors at concentration of 100, 50 or 10 µM for 30 minutes 100 ng/ml of LPS was then added to the cells and supernatants were collected after 16 hours and analysed for TNF-α production by ELISA.

As can be seen in FIG. 2A, 21 of the panel of 25 inhibitors were capable of reducing TNF-α production. At 100 µM 18 of these inhibitors were more effective than the commercially available MIF tautomerase inhibitor, ISO-1. TI 17 was most effective at 100 µM, reducing TNF-α production by over 70%. The commercially available MIF inhibitor, ISO-1 was found to reduce TNF-α by an average of 20%.

We also repeated this assay using both 50 µM and 10 µM of each of our panel of novel inhibitors and also ISO-1. FIG. 2B shows at 50 µM, approximately 13 compounds were more effective than the commercial standard ISO-1 (TI 17, 18, 13, 23, 12, 21, 22, 19, 8, 11, 16, 2, 7). Again TI 17 is the most effective at 50 µM and TI 18 was very effective without totally reducing TNF-α altogether. With pre-treatment of the inhibitor panel and ISO-1 at 10 µM, as can be seen from FIG. 2C, the reduction in TNF-α decreased however there were still 13 compounds (TIs-18, 23, 22, 21, 13, 12, 17, 11, 1, 20, 19, 25, 2) more effective than ISO-1.

As indicated vide supra of the 5 exemplary compounds shown in FIG. 3 TI 19 demonstrated the highest percentage inhibition of MIF enzymatic activity. Results from the TNF-α assay also show that TI 19 is more effective at reducing TNF-α than the commercially available ISO-1. TI 19 is one of the smallest of the 25 compounds which gives it a greater chance at being able get into the cell. Its structure has a number of different conformations it can adopt in order make the correct fit within the active site.

Effects of Compounds on PGE-2 Production in LPS Treated Cells

MIF has been shown to up-regulate COX-2 and in turn $PGE_2$ production. A study looking at rheumatoid arthritis showed that treating fibroblast-like synoviocytes (FLS) with recombinant MIF, significantly increased the amount of COX-2 activity and in turn the amount of $PGE_2$ production in the cells. Another study looked at the LPS induced COX-2 expression and also $PGE_2$ release in MIF-deficient macrophages; therein a significant reduction in $PGE_2$ release in the MIF-deficient macrophages in comparison to the $PGE_2$ production from wild type macrophages was reported.

It has also been shown that MIF plays a role in glucocorticoid regulation in activated monocytes. Macrophages which are treated with LPS are shown to have an increase in the expression of COX-2 and the production of $PGE_2$. This can be overridden with the addition of the anti-inflammatory dexamethasone. This was counteracted with the addition of recombinant MIF to this assay which was seen to restore the production of $PGE_2$ to the level seen by LPS treatment only. These findings support the hypothesis that inhibiting MIF will decrease its anti-inflammatory and also anti-tumour effects. MIF specific inhibitors have previously been shown to inhibit induced COX-2 production and $PGE_2$ release. Lubetsky et al (J Biol Chem, 2002. 277(28): p. 24976-82) showed that increasing concentrations of ISO-1 had the ability to reduce the production of PGE-2 in a dose dependant manner.

It has been previously shown that the level of LPS mediated PGE-2 release is 10-fold less in MIF deficient macrophages in comparison to that of Wild-Type macrophages and that the addition of recombinant MIF to these MIF deficient macrophages can help to restore the LPS mediated PGE-2 release. Thus inhibiting the enzymatic activity of MIF with our putative inhibitors should decrease the level of PGE-2 released from LPS treated cells.

The addition of exogenously applied LPS significantly increases the production of PGE-2 in comparison to untreated cells as can be seen from FIG. 4.

The ability of TI 19 to decrease the level of PGE-2 released from LPS treated cells was analysed by ELISA. Pre-treatment with TI 19 and ISO-1 significantly reduces this increase in LPS mediated PGE-2 production. Treatment with TI 19 caused a greater reduction in PGE-2 than ISO-1 at this concentration. At 100 µM concentration TI 19 reduced PGE-2 levels to comparable levels in untreated cells.

MIF and Lung Cancer

Effect of MIF Tautomerase Activity on Proliferation in Lewis Lung Cancer Tumour Cells MIF is also known to play a role in cellular proliferation. Studies have shown that MIF plays a role in the cell differentiation in the developing eye lens of chickens. Other studies found that MIF is found in the basal cells of the human epidermis, which are highly proliferative.

The role of MIF in the proliferation of T cells has also been investigated. Upon activation, T cells produce MIF and neutralising MIF with specific MIF antibodies can inhibit T-cell proliferation. This study also found that MIF was released in response to stimulation with glucocorticoids where it is found to override the glucocorticoid inhibition of proliferation of the T-cells indicating the antagonistic role of MIF and glucocorticoids in proliferation (Bacher et al. *Proc. Natl Acad. Sci. USA*, 1996. 93: p. 7849-7854).

Meyer-Siegler et al found an enhanced expression of MIF in both primary and metastatic prostate cancer cells (*Urology*, 1996. 48(3): p. 448-52). Following this finding, Takahashi et al went on to look at MIF involvement in the mechanism of tumour growth. They found that MIF was mainly localised in the cytoplasm of tumour cells and that by transfecting cells with an anti-sense MIF plasmid they were able to significantly inhibit cellular proliferation (Mol. Med., 1998. 4(11): p. 707-14).

rMIF added to fibroblasts induces significant proliferation while the addition of a monoclonal anti-MIF antibody reduces this proliferation (J Biol Chem, 1999. 274(25): p. 18100-6). Investigations were then carried out to determine if the enzymatic activity of MIF was involved in this process. Meyer-Siegler et al used the MIF inhibitor, ISO-1 to show that inhibition of enzymatic activity of MIF resulted in decreased cell proliferation in prostate cancer cells (J Immunol, 2006. 177(12): p. 8730-9).

We wanted to investigate the role of MIFs enzymatic activity in the proliferation of a tumour cell line. We looked at Lewis Lung carcinoma cells (LLC) which will be used in our tumour model study. It has been shown in a number of studies that MIF has the ability to inhibit apoptosis. It has also been shown that anti-MIF antibodies have the capacity to inhibit tumour cell proliferation. We hypothesised that by inhibiting MIF enzymatic activity that we would significantly reduce proliferation in these LLC-1 tumour cells.

MIF-KO and MIF-P1G Show Reduced Tumour Sized in Comparison to WT Mice

In order to establish if the enzymatic activity of MIF played a role in this particular lung cancer model, we looked at the comparison of tumour growth in mice which express normal levels of MIF (WT) with those that express a mutant MIF lacking enzymatic activity (P1G) and knockout MIF mice completely lacking MIF (MIF KO). This allowed a direct comparison of tumour growth in an environment which has MIF enzymatic activity and one without.

FIG. 7 shows that the MIF WT group was found to have a marked increase in tumour size from day 16 to 24 as would be expected. The average tumour size of the MIF KO group was 60% less at day 24 compared to the MIF WT group. The tautomerase null MIF P1G group had an average tumour size at day 24 that is 45% lower than that of the MIF WT group. The presence of the tautomerase null MIF in the P1G model shows a marked reduction in tumour size in comparison to the MIF-WT animals. This result is similar to reduction seen in complete MIF-KO mice, which suggests the enzymatic activity plays a substantial role in tumour growth in this model.

Effect of Compounds on Cellular Proliferation

The ability of candidate compounds to reduce cellular proliferation was also examined. For this assay, LLC cells were plated at a cell density of $5 \times 10^4$ cells/ml. The cells were then pre-treated with TI 19 or ISO-1 at a concentration of 100 μM. The cells were then treated with 100 ng/ml of recombinant MIF. The cells were incubated at 37° C. in a humidified 5% $CO_2$ incubator and after 48 hours the cells were harvested and counted. From FIG. 5 it can be seen that MIF promotes proliferation of Lewis lung carcinoma cells significantly relative to the untreated cells. ISO-1 reduced the MIF induced proliferation, but TI 19 reduced proliferation to levels comparable with untreated cells.

Effect of Compounds on Growth of Subcutaneous Tumour in Lung Cancer Model

MIF has been implicated in the pathogenesis of many types of cancer and is known to be over-expressed by tumours. It has been suggested that many unique biological functions of MIF are likely to contribute to an in vivo environment that favours the growth and invasiveness of tumours. Kamimura et al looked at the staining patterns of MIF protein in normal lung tissue in comparison to lung adenocarcinoma. They showed that there was increased MIF protein in the lung adenocarcinoma compared to normal lung tissue (Cancer, 2000. 89(2): p. 334-41). Furthermore, increased levels of MIF in lung cancer patients are associated with worse prognosis in lung cancer patients.

In order to assess the efficacy of inhibitors of MIF in lung cancer, we chose the Lewis lung carcinoma cell line (LLC) in vivo model. These cells were established from the lung of a C57BL mouse which had a tumour from the implantation of primary Lewis lung carcinoma. This cell line is commonly used for both the study of metastases and for studying potential cancer therapeutic compounds. A number of studies have used LLC cells in order to characterise the behaviour of lung cancer in vivo.

In order to assess the antitumour activity of the novel tautomerase inhibitors in vivo, a subcutaneous LLC-1 cell model was set up. The subcutaneous model was chosen so that tumours could be easily visualised and measured during the course of the experiment and to allow assessment of the growth of the tumour in real time. Lewis Lung carcinoma cells ($5 \times 10^5$) were injected sub-cutaneously into the left flank of C57BL/6 mice. Caliper measurements were taken twice weekly and tumour volume ($mm^3$) was calculated as $0.5 \times L \times W^2$. Tumour volume was found to increase over time, with exponential growth post day 22. The cut off point for this model was when the tumour measured 15 mm in diameter. This model gave us an indication of normal tumour growth in this subcutaneous model. It can be seen from this model that from day 22 to day 28 the size of the tumour grows considerably.

Effect of Candidate Compounds on Tumour Size in LLC-1 Model

Once it was determined that the enzymatic activity played a role in the growth of tumours, the subcutaneous LLC model was then used to assess the efficiency of the small weight molecular inhibitors. C57/B16 mice were injected intraperitoneally with 35 mg/kg of each of the inhibitors 30 minutes prior to subcutaneous tumour inoculation and again twice weekly for 4 weeks. Animals were monitored daily and tumour measurements taken until the tumour measured 15 mm in diameter.

As can be seen in FIG. 8 a significant reduction in tumour size was observed with the novel tautomerase inhibitor (TI 19) in comparison to the untreated group or vehicle treated group (DMSO). TI 19 reduced tumour growth by nearly 90% (116.1±30.41) in comparison to wild-type mice (1145±115.7). These novel findings highlight the importance of the tautomerase activity in this model.

Of the two compounds tested, we can see that TI 19 is more effective with over 90% reduction in tumour growth at day 28, with ISO-1 (a well known MIF inhibitor) resulting in over 50% reduction of tumour size. Our novel compound was approximately twice as effective in reducing tumour size as ISO-1 in the model at 28 days.

A similar trend was observed in the 7 day treatment model (FIG. 9). In this model, the tumour was allowed to progress until it became palpable on the flank of the mouse before treatment was initiated. Again, a significant reduction in tumour volume after the 28 day study is shown compared to ISO-1.

Structure Activity Relationship Studies

With a potent inhibitor of MIF tautomerase in hand we undertook structure activity relationship studies in order to ascertain the underlying activity of this compound class and to also investigate whether compounds with enhanced activity could be synthesized.

The structure of TI 19 is shown below:

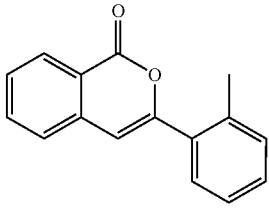
TI-19

The numbering of the ring system is depicted below:

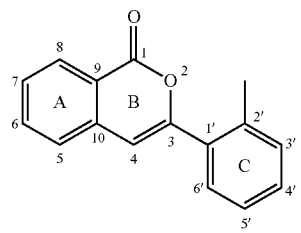
TI-19

Based on the results from the molecular modelling studies initially performed, at the outset of our SAR studies focus was placed on substitution of the aromatic ring at position 7 on the A ring.

The following analogues of TI 19 were synthesized

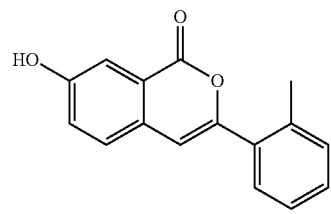
SDG-22

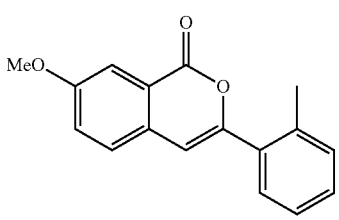
SDG-23

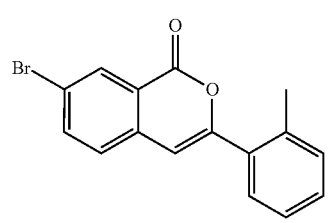
SDG-24

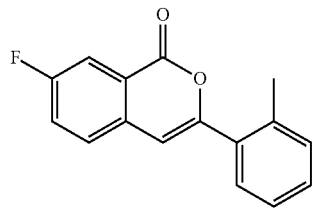
SDG-25

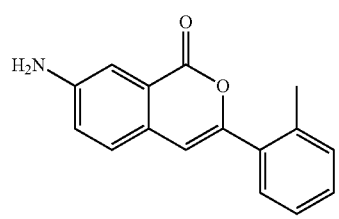
SDG-39

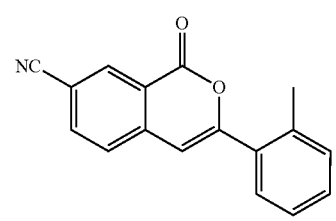
SDG-41

When the efficacy of the above compounds was examined in the tautomerase inhibition assay, SDG-22 proved to be a very effective inhibitor of MIF tautomerase.

SDG-22 differs from TI 19 in that it has a hydroxyl group in the 7-position. However, the presence of other substituents in the 7-position proved less effective than compound TI 19 at inhibiting the tautomerase activity of MIF.

The importance of the oxygen in the 2-position, was investigated by synthesizing the amino analogue of TI 19, compound SDG-42.

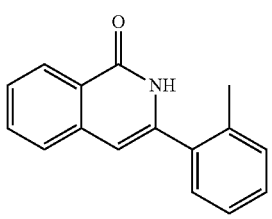
SDG-42

The presence of the oxygen proved critical to tautomerase inhibition activity as compound SDG-42 proved ineffective as a tautomerase inhibitor.

Similarly, the importance of the presence of the aromatic C ring was investigated by synthesizing SDG-40 below

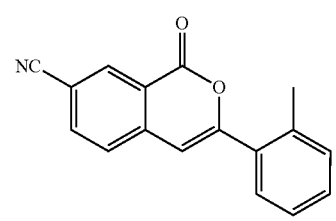
SDG-40

Removal of the aromatic C ring resulted in a dramatic loss of inhibitory activity.

With compound SDG-22 proving the most effective tautomerase inhibitor identified to date, several analogues of SDG-22 were synthesized.

The following compounds were synthesized:

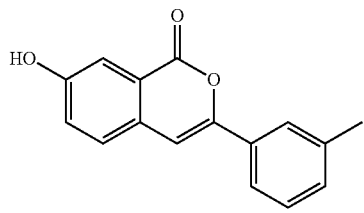
SDG-47

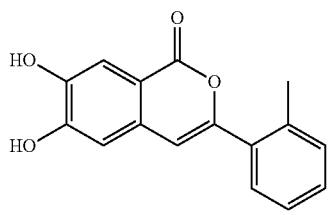
SDG-54

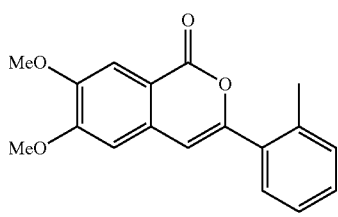
SDG-53

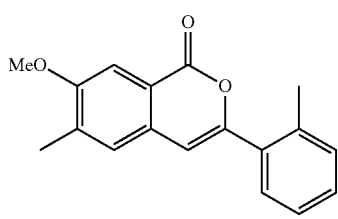
SDG-51

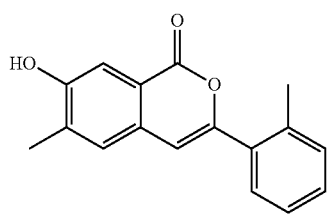
SDG-52

While SDG-52 displayed some inhibitory activity, SDG-47 and SDG-54 demonstrated almost complete inhibition of MIF tautomerase activity. Conversely, SDG-51, 53 and 23, which comprise a methoxy group in the 7-position did not significantly inhibit MIF tautomerase.

SDG-50, an analogue of TI 19 below demonstrates the effect of replacing the alkyl group in the 2'-position of the C ring with a hydroxyl group. A dramatic loss in tautomerase inhibition activity was observed.

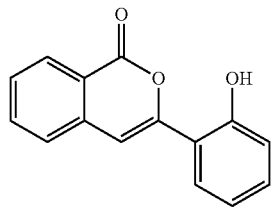
SDG-50

As is evident from the tautomerase inhibitory activity of SDG-22 and SDG 47, the presence of an alkyl group in either the 2' or 3' position of the C ring is important for tautomerase inhibitory activity. Replacing the 2' methyl with a hydroxyl group and removal of the 7-hydroxyl group resulted in a complete loss in inhibitory activity.

As can be seen from the inactivity of SDG-46, removal of an alkyl substituent from both the 2' and 3' positions of the C ring produces a class of compound which does not inhibit MIF tautomerase activity.

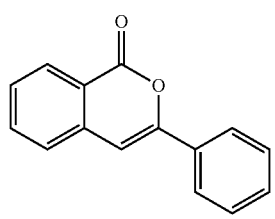
SDG-46

Conclusion

Herein, we disclose a new class of MIF inhibitor. Following a battery of in silico screening and docking studies, and biological evaluation of lead compounds in said docking studies, the isocoumarin compound TI 19 was identified as a potent inhibitor of MIF tautomerase which proved significantly more potent than the commercially available small molecule MIF inhibitor ISO-1.

TI 19 was shown to inhibit MIF tautomerase activity by 74% and led to a reduction in TNF-α production in LPS stimulated cells. TI 19 reduced cell proliferation in a lung cancer cell line and led to a significant reduction in tumour volume when assessed in a murine modil for lung cancer. Subsequent structure activity relationship studies identified compound SDG-22, a compound significantly more potent than TI 19, which inhibited MIF tautomerase activity by >90% and caused a significant reduction in TNF-α production in LPS stimulated RAW macrophage murine cells. In a comparative analysis SDG-22 reduced TNF-α production in LPS stimulated RAW macrophage murine cells by 97%, which proved 80% more effective than the known MIF inhibitor ISO-1 and 10% more effective than TI 19 in the same assay.

Structure activity relationship studies identified the 7-hydroxyl group of SDG-22 as being essential to its enhanced activity. The mere replacement of said 7-hydroxyl group with a methoxy group in the same position leads to almost a complete loss in tautomerase inhibitory activity.

The presence of a 6-hydroxyl group also proved tolerable and SDG-54 proved to inhibit MIF tautomerase to 86%.

Investigation as to the importance of substitution about the C ring of the isocoumarin structure, revealed the importance of the presence of an alkyl group in the 2' or 3' position in addition to the hydroxyl group in the 7-position. Replacement of said 2' alkyl group, with a hydroxyl group, in the absence of a 3' substituent, leads to almost a complete loss in activity. When both the 2' and 3' are hydrogen, a dramatic loss in activity was observed.

Synthesis of Representative Isocoumarin Compounds

Homophthalic Acid Route:

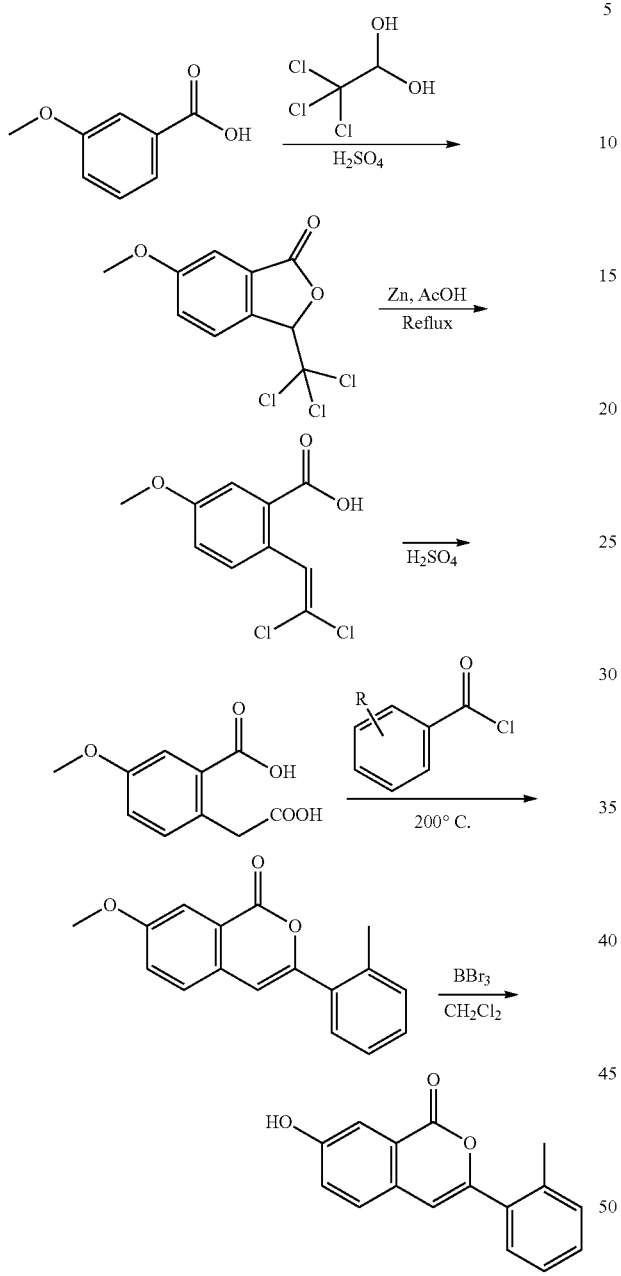

o-Halobenzoic Acid Route:

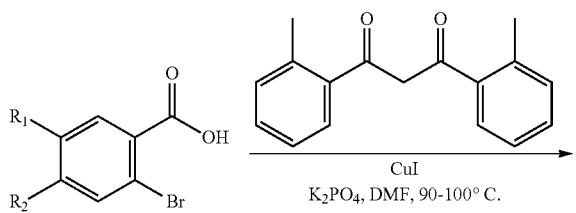

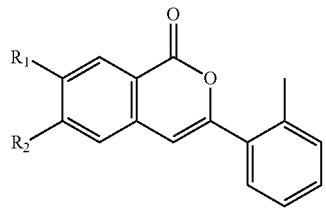

Isocoumarins were synthesized either via the route described by Cai et al. (JOC, 2012, 77, 2331-2336) or through the direct reaction of homophtalic acids and the corresponding acyl chloride derivative. The 7-methoxyisocoumarin was synthesized by the route described by Cornaggia et al. (Org Lett, 2012, 14, 1850-1853, see above)

General Procedure for Synthesis of Isocoumarins:

Method A:

Homophtalic acid (0.5 mmol, 1 equiv.) and acyl chloride (2 mmol, 4 equiv.) were stirred at 200° C. for 6 h. The reaction was allowed to cool and diluted with CH$_2$Cl$_2$ and water. The layers were separated and the aqueous layer extracted into CH$_2$Cl$_2$. The combined organic layers were washed with NaHCO$_3$ (sat.), brine and dried over MgSO$_4$. The solvents were removed under reduced pressure and the residue was purified via flash chromatography (Hex:EtOAc, 9:1) to give the desired compound.

Method B: (JOC, 2012, 77, 2331-2336)

A microwave vial was charged with the mixture of o-halobenzoic acid (0.5 mmol), 1,3-diketone 2 (0.5 mmol), CuI (0.05 mmol), and K$_3$PO$_4$ (1.0 mmol), and the mixture was then stirred in DMF (1 mL) The tube was sealed and the mixture was heated in a microwave for 1-2 hours. After completion, the mixture was cooled to room temperature. Water was then added, and the mixture was extracted with EtOAc, dried over MgSO$_4$ and concentrated under reduced pressure. Flash purification of the residue gave the desired isocoumarin compound.

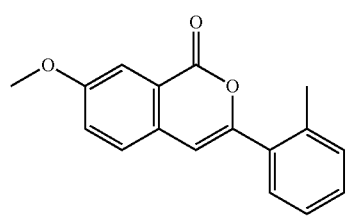 [SMILES: COc1ccc2cc(-c3ccccc3C)oc(=O)c2c1]

3-(2'-methylphenyl)-7-methoxyisocoumarin (SDG-21)

Synthesised via method B (46 mg, 35% yield); $^1$H NMR (400 MHz, CDCl$_3$) δ 7.72 (s, 1H), 7.48 (d, J 7.2 Hz, 1H), 7.39 (d, J 8.3 Hz, 1H), 7.30 (d, J 7.3 Hz, 1H), 7.25 (d, J 7.3 Hz, 1H), 6.55 (s, 1H), 3.90 (s, 3H), 2.48 (s, 3H); $^{13}$C NMR (101 MHz, CDCl$_3$) δ 158.17, 136.43, 132.82, 131.06, 130.97, 129.44, 129.09, 127.66, 125.92, 119.29, 107.75, 105.68, 55.84, 20.53; ESI-HRMS calcd for C$_{17}$H$_{15}$O$_3$ 267.1021. found m/z 267.1012 [M+H]$^+$.

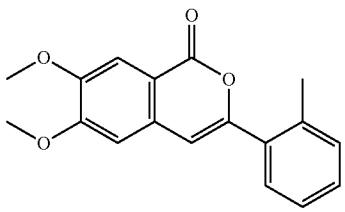 [SMILES: COc1cc2cc(-c3ccccc3C)oc(=O)c2cc1OC]

3-(2'-methylphenyl)-6,7-dimethoxyisocoumarin (SDG-53)

Synthesised via method B (29 mg, 20% yield); $^1$H NMR (400 MHz, CDCl$_3$) δ 7.68 (s, 1H), 7.49 (d, J 7.7 Hz, 1H), 7.35-7.29 (m, 1H), 7.28-7.21 (m, 3H), 6.84 (s, 1H), 6.53 (s, 1H), 4.00 (s, 3H), 3.99 (s, 4H), 2.49 (s, 3H); $^{13}$C NMR (101 MHz, CDCl$_3$) δ 162.4, 155.1, 149.7, 136.6, 132.7, 130.9, 129.5, 129.1, 125.9, 113.4, 109.4, 106.3, 105.6, 56.3, 56.2, 20.7; ESI-HRMS calcd for C$_{18}$H$_{17}$O$_4$297.1126. found m/z 297.1124 [M+H]$^+$.

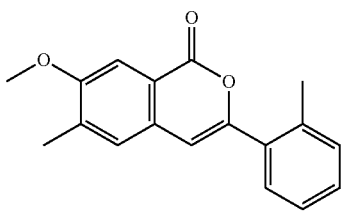 [SMILES: COc1cc2c(=O)oc(-c3ccccc3C)cc2cc1C]

3-(2'-methylphenyl)-6-methyl-7-methoxyisocoumarin (SDG-51)

Synthesised via method B (35 mg, 25% yield) $^1$H NMR (400 MHz, CDCl$_3$) δ 7.64 (s, 1H), 7.49 (d, J 7.5 Hz, 1H), 7.32 (m, 1H), 7.24 (m, 3H), 6.52 (s, 1H), 3.94 (s, 3H), 2.48 (s, 3H), 2.34 (s, 3H); $^{13}$C NMR (101 MHz, CDCl$_3$) δ 158.1, 136.4, 132.8, 131.0, 130.9, 129.4, 129.0, 127.6, 125.8, 119.2, 107.7, 105.6, 55.8, 20.5, 16.8; ESI-HRMS calcd for C$_{18}$H$_{17}$O$_3$ 281.1177 found m/z 281.1170 [M+H]$^+$.

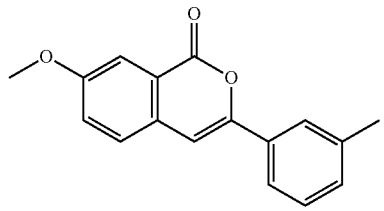

3-(3'-methylphenyl)-7-methoxyisocoumarin (SDG-43)

Synthesised via method A (66 mg, 50% yield); $^1$H NMR (400 MHz, CDCl$_3$) δ 8.28 (s, 1H), 7.67 (m, 2H), 7.48 (m, 2H), 7.33 (t, J 7.7 Hz, 1H), 7.27-7.18 (m, 1H), 6.92 (s, 1H), 3.94 (s, 3H), 2.41 (s, 3H); $^{13}$C NMR (101 MHz, CDCl$_3$) δ 162.3, 153.7, 138.5, 137.5, 134.8, 131.8, 130.7, 129.6, 128.6, 128.0, 125.8, 122.3, 120.4, 101.6, 55.7, 21.4; ESI-HRMS calcd for C$_{17}$H$_{15}$O$_3$ 267.1021. found m/z 267.1018 [M+H]$^+$.

General Procedure for Methyl Ether Cleavage:

A solution of boron tribromide (0.6 mmol, 1M in CH$_2$Cl$_2$) was added to isocoumarin derivative (0.1 mmol) in CH$_2$Cl$_2$ (2.5 mL) at 0° C. The reaction was stirred at room temperature for 16 h. Na$_2$CO$_{3(sat.)}$ was added and the reaction was diluted with EtOAc. Phases were separated and the aqueous phase was acidified with 1M HCl, extracted into EtOAc. The combined organic phases were dried over MgSO$_4$ and the solvents were removed under reduced pressure. Flash purification of the residue (Hex:EtOAc 6:1) gave the desired compounds.

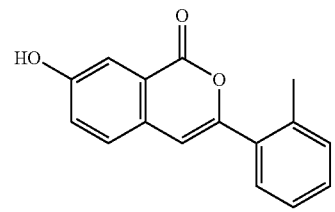 [SMILES: Cc1ccccc1-c1cc2ccc(O)cc2c(=O)o1]

3-(2'-methylphenyl)-7-hydroxyisocoumarin (SDG-22)

(20 mg, 85% yield) $^1$H NMR (400 MHz, CDCl$_3$) δ 7.95 (s, 1H), 7.48 (d, J 7.4 Hz, 1H), 7.41-7.28 (m, 4H), 7.24 (s, 2H), 6.60 (s, 1H), 2.48 (s, 3H); $^{13}$C NMR (101 MHz, CDCl$_3$) δ 158.1, 136.4, 132.8, 131.1, 130.9, 129.4, 129.09, 127.6, 126.0, 119.3, 107.7, 105.6, 20.5; ESI-HRMS calcd for C$_{16}$H$_{13}$O$_3$ 253.0864. found m/z 253.0872 [M+H]$^+$.

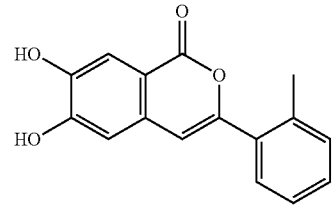 [SMILES: Cc1ccccc1-c1cc2cc(O)c(O)cc2c(=O)o1]

3-(2'-methylphenyl)-6,7-hydroxyisocoumarin (SDG-54)

(2 mg, 83% yield); $^1$H NMR (400 MHz, CD$_3$OD) δ 7.58 (s, 1H), 7.49 (d, J 7.5 Hz, 1H), 7.32 (tt, J 14.3, 7.4 Hz, 3H), 6.96 (s, 1H), 6.67 (s, 1H), 2.47 (s, 3H); ESI-HRMS calcd for C$_{16}$H$_{13}$O$_4$ 269.0813. found m/z 269.0824 [M+H]$^+$.

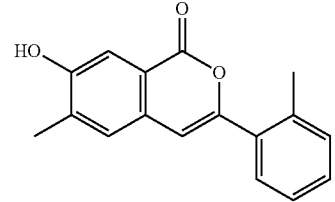 [SMILES: Cc1cc2cc(-c3ccccc3C)oc(=O)c2cc1O]

3-(2'-methylphenyl)-6-methyl-7-hydroxyisocoumarin (SDG-52)

(6 mg, 80% yield); $^1$H NMR (400 MHz, CDCl$_3$) δ 7.55 (s, 1H), 7.48 (s, 1H), 7.39 (d, J 7.6 Hz, 1H), 7.26-7.14 (m, 5H), 6.55 (s, 1H), 2.38 (s, 3H), 2.28 (s, 3H); ESI-HRMS calcd for $C_{17}H_{15}O_3$ 267.1021. found m/z 267.1028 [M+H]$^+$.

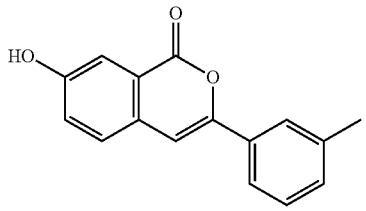 [SMILES: Cc1cccc(-c2cc3ccc(O)cc3c(=O)o2)c1]

3-(3'-methylphenyl)-7-hydroxyisocoumarin
(SDG-47)

(15 mg, 84% yield); $^1$H NMR (400 MHz, CDCl$_3$) δ 7.90 (s, 1H), 7.49-7.26 (m, 5H), 7.24 (s, 2H), 6.60 (s, 1H), 2.45 (s, 3H); $^{13}$C NMR (101 MHz, CDCl$_3$) δ 158.2, 136.3, 132.5, 131.3, 130.7, 129.2, 129.0, 127.2, 126.1, 120, 107.2, 105.3, 20.65; ESI-HRMS calcd for $C_{16}H_{13}O_3$ 253.0864. found m/z 253.0866 [M+H]$^+$.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A compound having the formula:

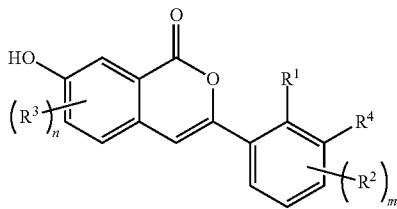

wherein n is 3; m is 0 to 3;
$R^1$ and $R^4$ are the same or different and are independently selected from the group consisting of hydrogen and $C_1$-$C_{12}$ aliphatic;
wherein $R^1$ and $R^4$ can independently be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, or oxo; wherein each R' is independently selected from the group consisting of hydrogen and $C_1$-$C_6$ alkyl;

$R^2$ is independently selected from the group consisting of hydrogen, an amino group, a halogen, a cyano group, a nitro group, a nitroso group, and $C_1$-$C_{12}$ aliphatic;
$R^3$ is hydrogen;
wherein, independently any $R^2$ can be unsubstituted, or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, or oxo; wherein R' is independently selected, for each occurrence, from the group consisting of hydrogen and $C_1$-$C_6$ alkyl;
wherein $R^1$ and $R^4$ are not simultaneously hydrogen;
or pharmaceutically acceptable salts thereof or pharmaceutically acceptable hydrates thereof.

2. The compound as claimed in claim 1, wherein $R^1$ is $C_1$-$C_{12}$ aliphatic; which can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, or oxo; wherein each R' is independently selected from the group consisting of hydrogen and $C_1$-$C_6$ alkyl; and $R^4$ is hydrogen.

3. The compound as claimed in claim 1, wherein $R^4$ is $C_1$-$C_{12}$ aliphatic; which can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, or oxo; wherein each R' is independently selected, from the group consisting of hydrogen and $C_1$-$C_6$ alkyl; and $R^1$ is hydrogen.

4. The compound as claimed in claim 1, wherein $R^1$ and $R^4$ are independently $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, or oxo; wherein R' is independently selected, for each occurrence, from the group consisting of hydrogen and $C_1$-$C_6$ alkyl.

5. The compound as claimed in claim 1, wherein $R^1$ is selected from the group consisting of methyl, ethyl, propyl, isopropyl, butyl, isobutyl, sec-butyl, pentyl, hexyl, heptyl and octyl and $R^4$ is hydrogen.

6. The compound as claimed in claim 1, wherein $R^4$ is selected from the group consisting of methyl, ethyl, propyl, isopropyl, butyl, isobutyl, sec-butyl, pentyl, hexyl, heptyl and octyl and $R^1$ is hydrogen.

7. The compound as claimed in claim 1, wherein $R^1$ and $R^4$ are independently selected from the group consisting of methyl, ethyl, propyl, isopropyl, butyl, isobutyl, sec-butyl, pentyl, hexyl, heptyl and octyl.

8. The compound as claimed in claim 1 having the formula:

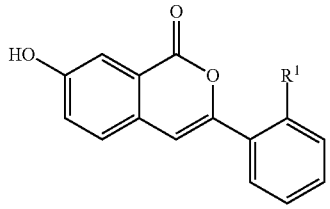

wherein $R^1$ is selected from the group consisting of $C_{1-12}$ alkyl; wherein $C_{1-12}$ alkyl can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl or oxo; wherein R' is independently selected, for each occurrence, from the group consisting of hydrogen and $C_1$-$C_6$ alkyl.

9. The compound as claimed in claim 1 having the formula:

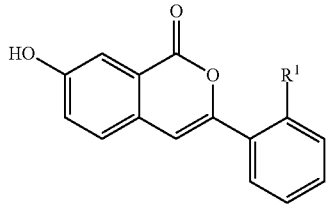

wherein $R^1$ is $C_{1-12}$ alkyl; which can be unsubstituted or substituted with at least one of a fluorine, chlorine, bromine, or iodine.

10. The compound as claimed in claim 1, wherein $R^1$ is selected from the group consisting of methyl, ethyl, propyl, butyl, pentyl, hexyl, isopropyl, —CFH$_2$, —CF$_2$H, —CF$_3$, and —CH$_2$CF$_3$.

11. The compound as claimed in claim 1 having the formula:

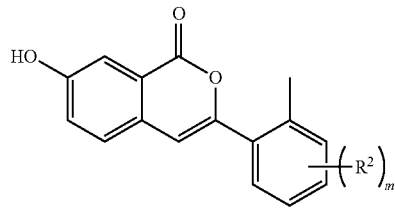

wherein any $R^2$ is independently selected from the group consisting of hydrogen, an amino group, a halogen, a cyano group, a nitro group, a nitroso group, and $C_1$-$C_{12}$ aliphatic;

wherein $R^2$ can be unsubstituted or substituted with at least one of a halogen, a hydroxyl, an amino group, a sulfonyl group, a sulphonamide group, a thiol, a $C_1$-$C_6$ alkyl, a $C_1$-$C_6$ alkoxy, a $C_1$-$C_6$ ether, a $C_1$-$C_6$ thioether, a $C_1$-$C_6$ ester, a $C_1$-$C_6$ ketone, a $C_1$-$C_6$ ketimine, a $C_1$-$C_6$ sulfone, a $C_1$-$C_6$ sulfoxide, a $C_1$-$C_6$ primary amide, a $C_1$-$C_6$ secondary amide, a halo $C_1$-$C_6$ alkyl, a carboxyl group, a cyano group, a nitro group, a nitroso group, —C(O)O—$C_1$-$C_6$ alkyl, —OC(O)O—$C_1$-$C_6$ alkyl, —OC(O)NR'R', —N(R')C(O)NR'R', —N(R')C(O)O—$C_1$-$C_6$ alkyl, or oxo; wherein any R' is independently selected, for each occurrence, from the group consisting of hydrogen and $C_1$-$C_6$ alkyl.

12. A compound having the formula:

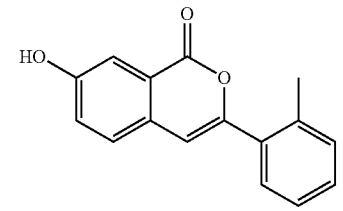

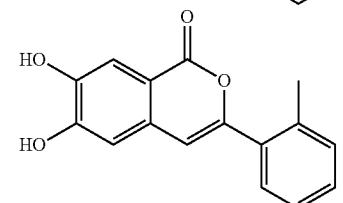

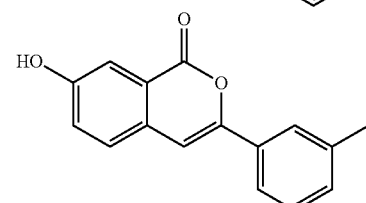

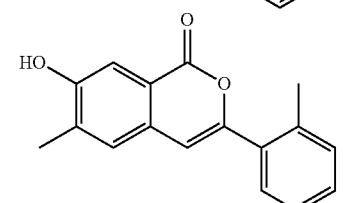

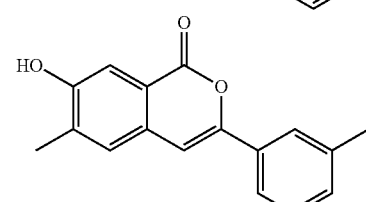

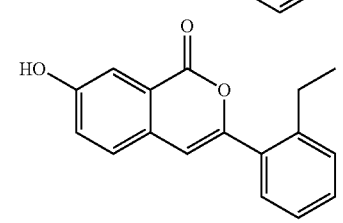

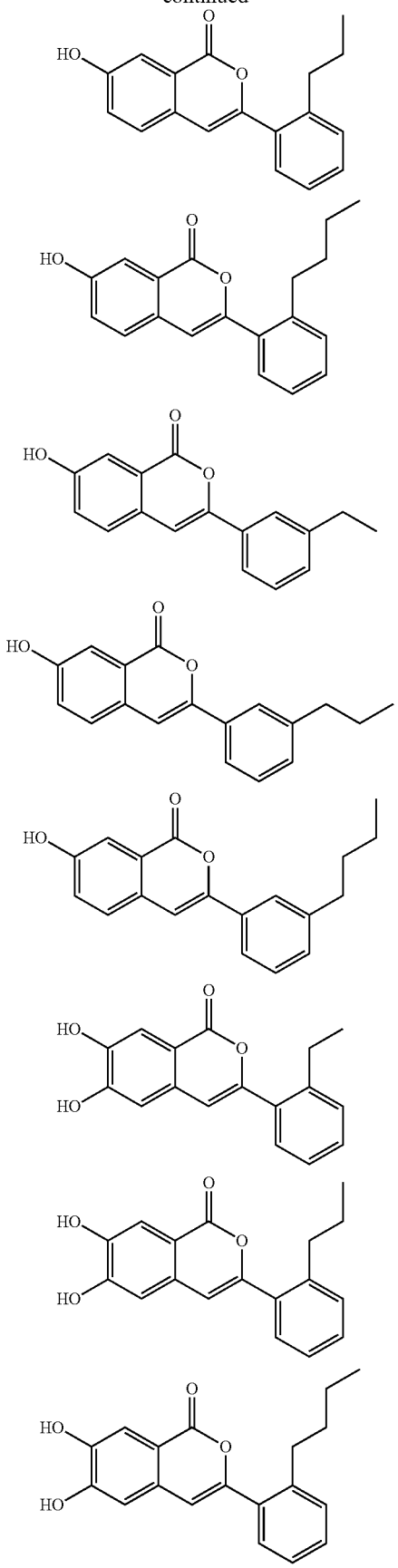
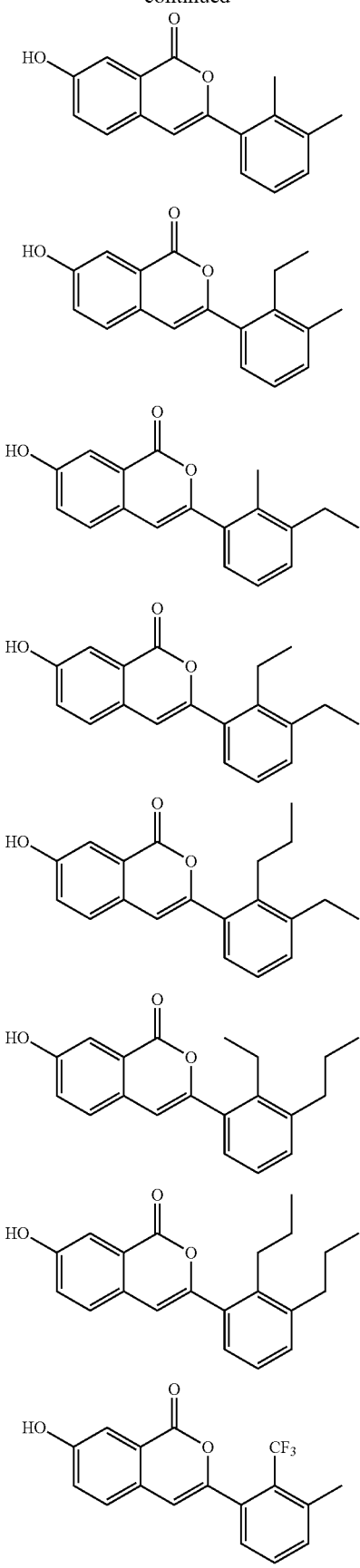

-continued

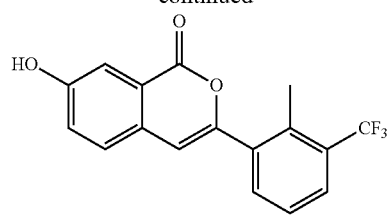
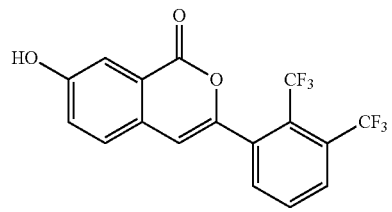
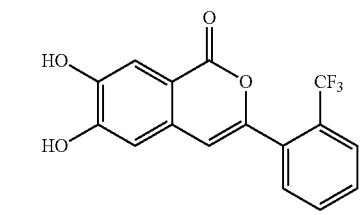
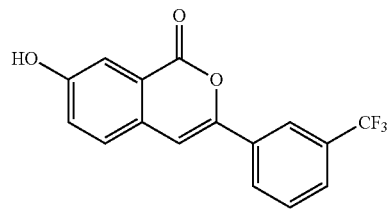
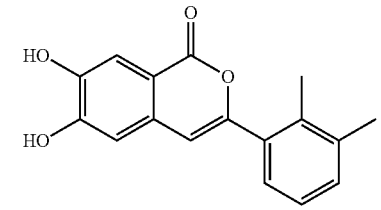
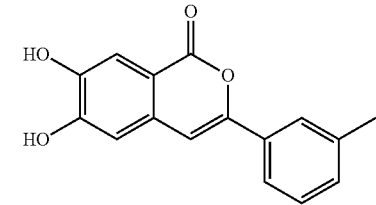
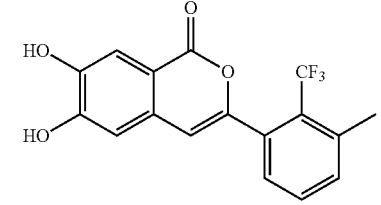
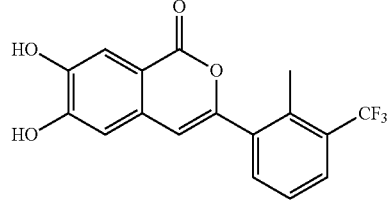

-continued

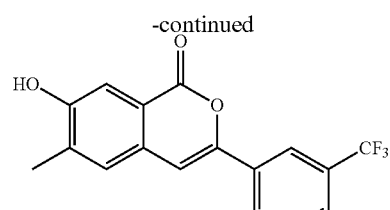
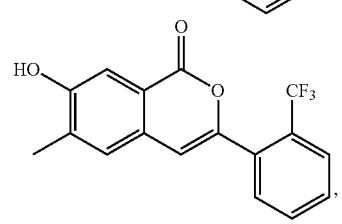

or a pharmaceutically acceptable salt thereof or a pharmaceutically acceptable hydrate thereof.

13. The compound according to claim 12 having the formula:

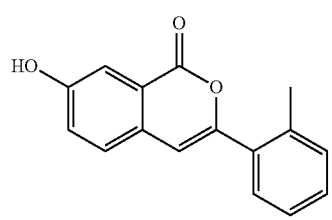
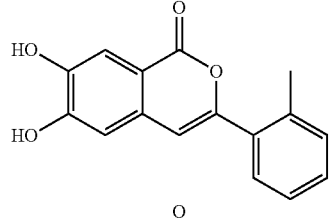
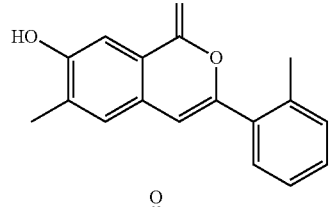
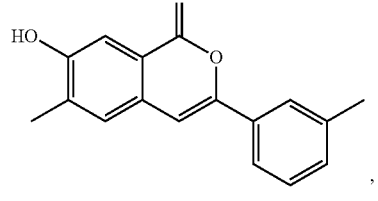

or a pharmaceutically acceptable salt thereof or a pharmaceutically acceptable hydrate thereof.

14. A pharmaceutical composition comprising the compound, or pharmaceutically acceptable salt thereof or pharmaceutically acceptable hydrate thereof according to claim 1 and at least one pharmaceutically acceptable carrier or excipient.

15. A method of treating cancer, comprising administering to a patient a therapeutically effective amount of the compound, a pharmaceutically acceptable salt thereof or pharmaceutically acceptable hydrate thereof according to claim 1.

16. The method according to claim 15, wherein the cancer is selected from the group consisting of: lung cancer, ovarian cancer, breast cancer, hepatocellular cancer, oesophageal squamous-cell cancer, bladder cancer, cervical squamous-cell cancer, pancreatic cancer, glioblastomas, prostate cancer, osteosarcoma, colorectal cancer, head and neck cancer and malignant melanoma, gastric cancer, glioma, and nasopharyngeal cancer.

17. The method of claim 16, wherein the cancer is lung cancer.

18. The method of claim 16, wherein the cancer is breast cancer.

* * * * *

UNITED STATES PATENT AND TRADEMARK OFFICE
CERTIFICATE OF CORRECTION

PATENT NO. : 10,106,519 B2  
APPLICATION NO. : 15/129593  
DATED : October 23, 2018  
INVENTOR(S) : Seamas Donnelly et al.

Page 1 of 1

It is certified that error appears in the above-identified patent and that said Letters Patent is hereby corrected as shown below:

On the Title Page

Column 1, Item (71) Applicant, Line 3, after "Holy," insert -- and Undivided Trinity of Queen Elizabeth, --

In the Claims

Column 48, Claim 13, Lines 48-57, delete " 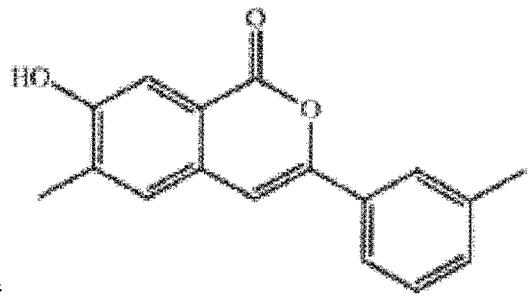 " and insert -- 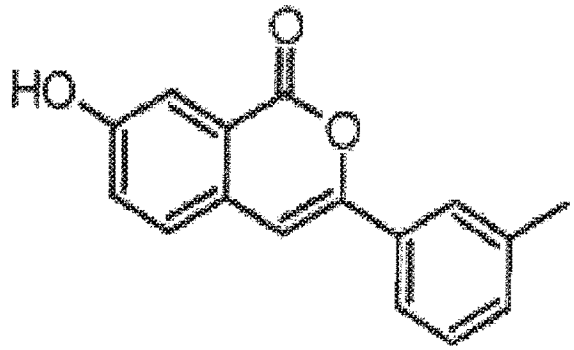 --

Column 49, Line 1, Claim 15, before "pharmaceutically" delete "a"

Signed and Sealed this  
Twenty-second Day of January, 2019

Andrei Iancu  
*Director of the United States Patent and Trademark Office*